US009234825B2

(12) United States Patent  
Huang et al.

(10) Patent No.: US 9,234,825 B2  
(45) Date of Patent: Jan. 12, 2016

(54) METHOD AND APPARATUS FOR FATIGUE AND VISCOELASTIC PROPERTY TESTING OF ASPHALT MIXTURES USING A LOADED WHEEL TESTER

(75) Inventors: Baoshan Huang, Knoxville, TN (US); Xiang Shu, Knoxville, TN (US); Hao Wu, Changsha (CN)

(73) Assignee: University of Tennessee Research Foundation, Knoxville, TN (US)

(*) Notice: Subject to any disclaimer, the term of this patent is extended or adjusted under 35 U.S.C. 154(b) by 959 days.

(21) Appl. No.: 13/433,465

(22) Filed: Mar. 29, 2012

(65) Prior Publication Data

US 2012/0253704 A1    Oct. 4, 2012

Related U.S. Application Data

(60) Provisional application No. 61/468,912, filed on Mar. 29, 2011.

(51) Int. Cl.
   *G01N 33/42*      (2006.01)
   *G01N 3/32*       (2006.01)

(52) U.S. Cl.
   CPC .............. *G01N 3/32* (2013.01); *G01N 33/42* (2013.01); *G01N 2203/0073* (2013.01); *G01N 2203/0094* (2013.01)

(58) Field of Classification Search
   CPC .. G01N 3/32; G01N 33/42; G01N 2203/0094
   USPC .................................................... 702/43, 42
   See application file for complete search history.

(56) References Cited

U.S. PATENT DOCUMENTS

| | | | |
|---|---|---|---|
| 5,248,200 A * | 9/1993 | Walsh | 374/45 |
| 5,614,670 A | 3/1997 | Nazarian et al. | |
| 5,659,140 A * | 8/1997 | Jakob et al. | 73/788 |
| 5,900,556 A * | 5/1999 | Ahmad et al. | 73/800 |
| 5,969,261 A * | 10/1999 | McAlister et al. | 73/813 |
| 6,053,052 A * | 4/2000 | Starostovic | 73/851 |
| 6,408,683 B2 | 6/2002 | Bahia et al. | |
| 7,374,659 B1 * | 5/2008 | Burris et al. | 208/22 |
| 2002/0043099 A1 * | 4/2002 | Maruoka et al. | 73/54.39 |
| 2003/0188585 A1 * | 10/2003 | Esser et al. | 73/826 |
| 2004/0177678 A1 * | 9/2004 | Grehlinger et al. | 73/54.01 |
| 2010/0139350 A1 * | 6/2010 | Smith et al. | 72/11.2 |
| 2010/0316445 A1 * | 12/2010 | Kasahara et al. | 404/77 |

OTHER PUBLICATIONS

Fakhri, M. (1997). "Characterisation of Asphalt Pavement Materials," Ph.D. Thesis, The University of New South Wales, Sydney, Australia, 331 pages.
Strategic Highway Research Program (SHRP) A-404 (1994), Fatigue Response of Asphalt-Aggregate Mixes, 310 pages.

(Continued)

*Primary Examiner* — Gregory J Toatley  
*Assistant Examiner* — Terence Stifter, Jr.

(57) ABSTRACT

A loaded wheel tester for testing asphalt mixtures comprises a loaded wheel tester having additional means for attachment to specimens under test to provide a measurement of tensile strain and for attachment between a frame of the loaded wheel tester and the loaded wheel to determine position of the loaded wheel over time. Output results demonstrate that viscoelastic and fatigue properties of asphalt mixtures are obtained in equivalent or improved format using a modified loaded wheel tester when compared with known pavement test apparatus and methods.

13 Claims, 29 Drawing Sheets

(a) top view (b) side view

Schematic diagram of APA loading system

(56) References Cited

OTHER PUBLICATIONS

Carpenter, S.H., and Jansen, M. (1997). "Fatigue Behavior Under New Aircraft LoadingConditions." Proceedings of Aircraft Pavement Technology in the Midst of Change, pp. 259-271.

Baburamani, P. S., and Porter, D. W. (1996). "Dissipated Energy Approach to Fatigue Characterisation of Asphalt Mixes." Proceeding of Combined 18th ARRB TR Conference Transit New Zealand Symposium, Part 2, pp. 327-347.

Tayebali, Akhtarhusein, et al (1992). "Modeling Fatigue Response of Asphalt-Aggregate Mixtures." Proceedings of Asphalt PAving Technologists, vol. 62, pp. 385-421.

Van Dijk and Visser (1977). "The Energy Approach to Fatigue for Pavement Design." Proceedings of Annual Meeting of the Association of Asphalt PAving Technologists (AAPT), vol. 46, pp. 1-40.

Aashto, (2007) "T 321-07: Determining the Fatigue Life of Compacted Hot-Mix Asphalt (HMA) Subject to Repeated Flexural Bending." Standard Specifications for Transportation Materials and Methods of Sampling and Testing, Part II, American Association of State Highway and Transportation Officials, Washington D.C.

Aashto, (2007), "T 322: Standard Method of Test for Determining the Creep Compliance and Strength of Hot-Mix Asphalt (HMA) Using the Indirect Tensile Test Device." American Association of State Highway and Transportation Officials, Washington D.C.

ASTM D 7460, Standard Test Method for Determining Fatigue Failure of Compacted Asphalt Concrete Subjected to Repeated Flexural Bending, 2010, 14 pages.

Carpenter, S.H., Ghuzlan, K., and Shen, S. (2003) "A Fatigue Endurance Limit for Highway and Airport Pavements." Transportation Research Record 1832, Transportation Research Board, Washington D. C., pp. 1-17.

Ghuzlan, K, and Carpenter, S.H. (2000). "An Energy-Derived/Damage-Based Failure Criteria for Fatigue Testing." Transportation Research Record 1723, Transportation Research Board, Washington D. C., pp. 141-149.

Lytton, "Characterizing Asphalt Pavements for Performance," Transportation Research Record: Journal of the Transportation Research Board, (2000), Paper No. 002000-2878, pp. 2-90.

Shen, S., and Carpenter, S.H. (2005). "Application of Dissipated Energy Concept in Fatigue Endurance Limit Testing." Transportation Research Record, Issue:1929: 165-173.

Shen, S., (2006). "Dissipated energy concepts for HMA performance: Fatigue and healing". Ph.D. Thesis, University of Illinois atUrbana-Champaign, Urbana, IL.

Strategic Highway Research Project (SHRP) A-003A, "Summary Report of Fatigue Response of Asphalt Mixtures," 1990, 158 pages.

Pavement Technology Inc. (PTI), Covington, GA. "Asphalt Pavement Analyzer (APA) User's Guide: For Use with all PC Controlled APA's," Nov. 2003 pp. 1-50.

\* cited by examiner

Schematic of LWT Fatigue Testing (Prior Art)

(a) Early version of APA (b) Lead wires attached to bottom surface

Early version of APA for fatigue testing (Prior Art)

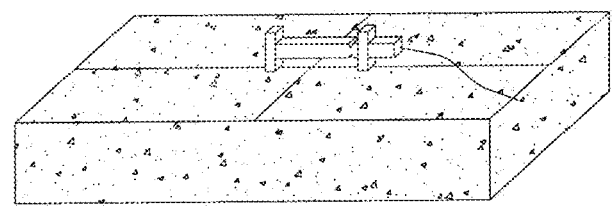
(a) Beam specimen with LVDT
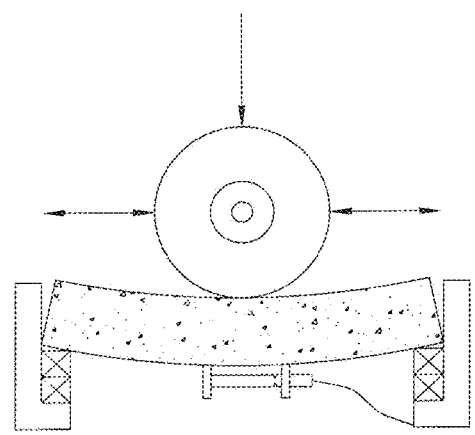
(b) Beam specimen in testing position
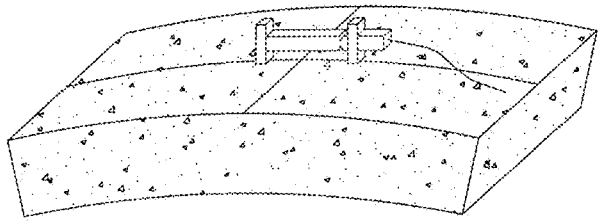
(c) Beam specimen after fatigue failure
FIG. 3
LWT fatigue and viscoelastic property test

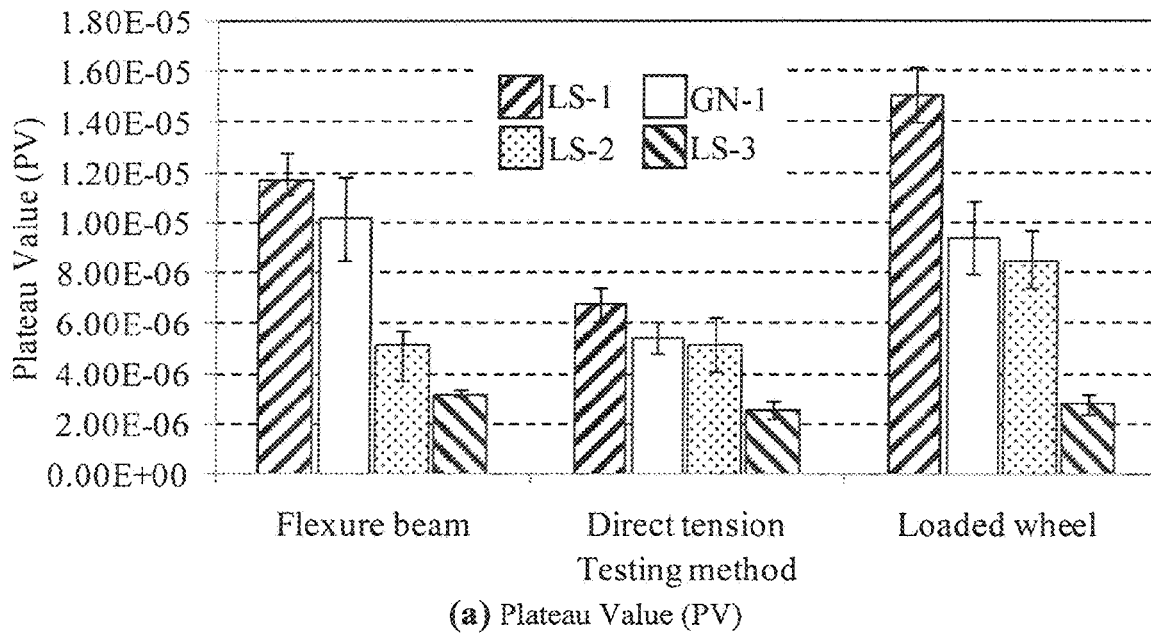
(a) Plateau Value (PV)
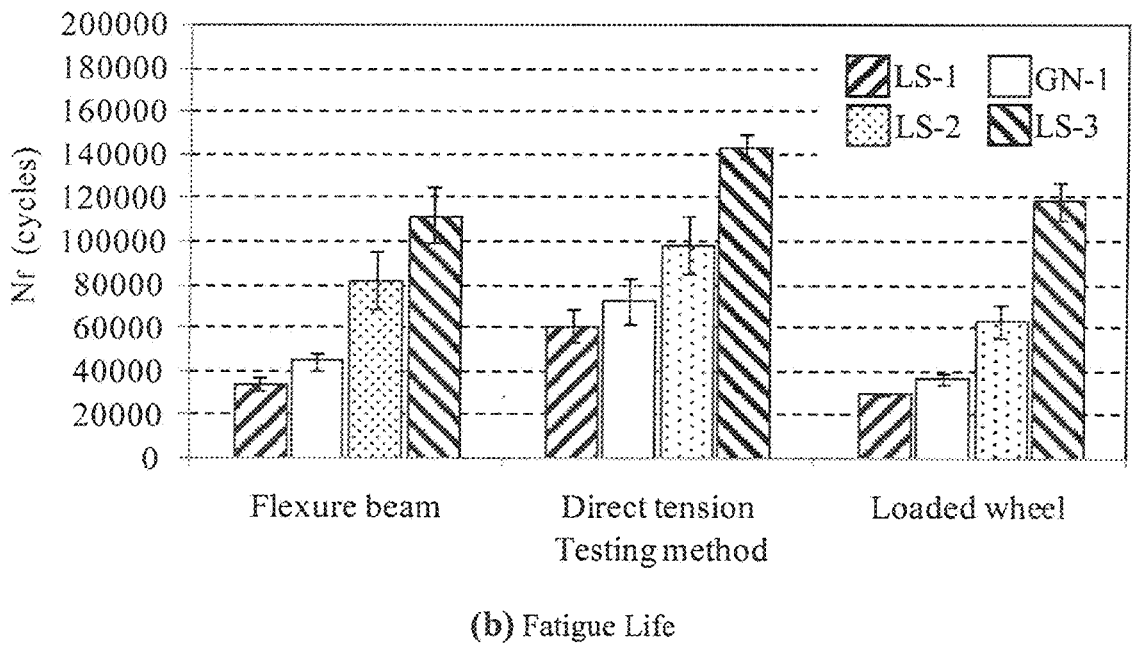
(b) Fatigue Life
FIG. 4
Comparison of Results from the Three Fatigue Tests

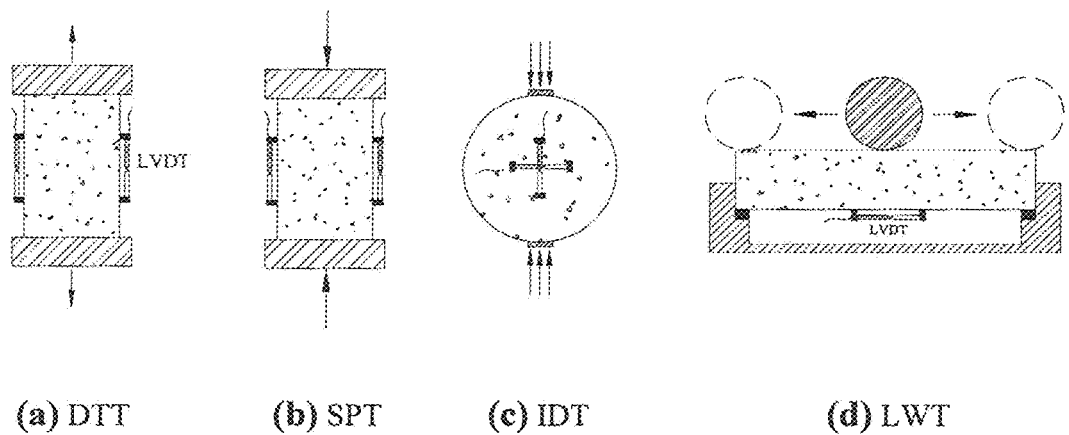
(a) DTT    (b) SPT    (c) IDT    (d) LWT
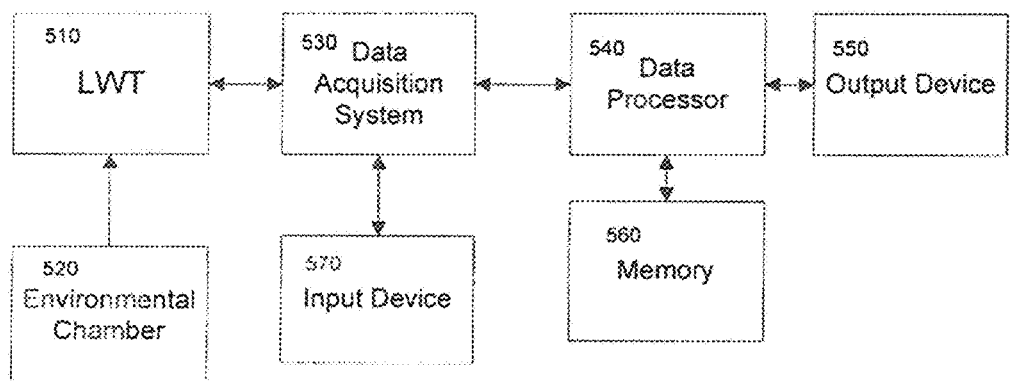
(e) Simplified Block Diagram of Modified Loaded Wheel Tester
FIG. 5
Various tests for viscoelastic properties of asphalt mixture

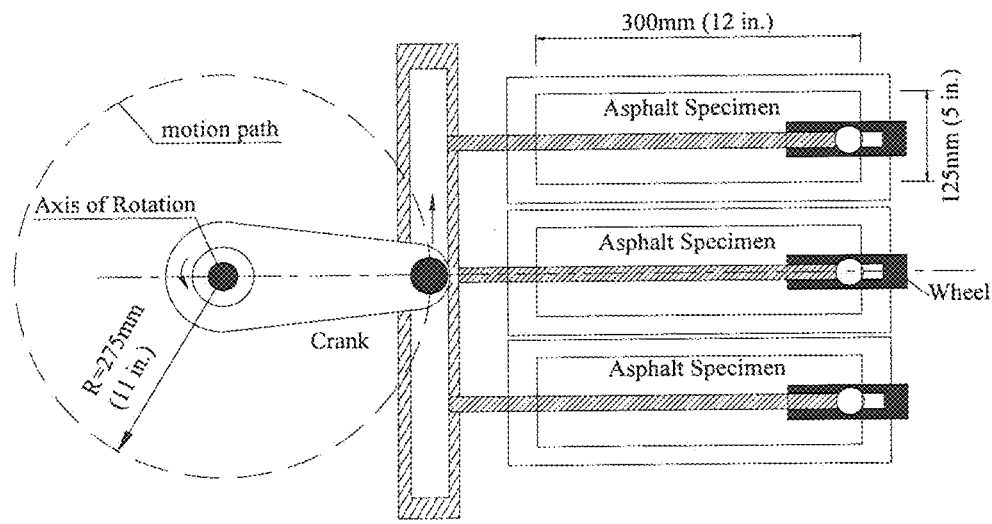
(a) top view
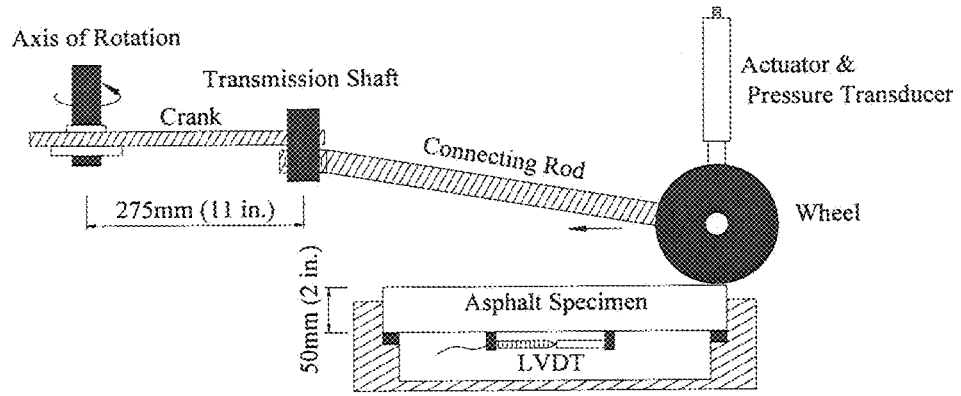
(b) side view
FIG. 6
Schematic diagram of APA loading system Establishment of movement equation Movement function of APA loading system (Tr = 1s)

Simplified mechanical model for stress analysis

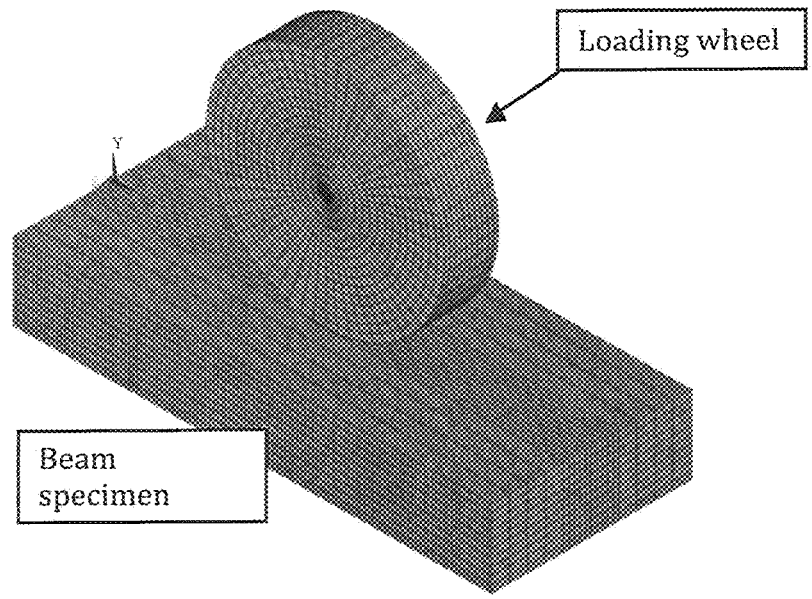
(a) 3-D FE structural model
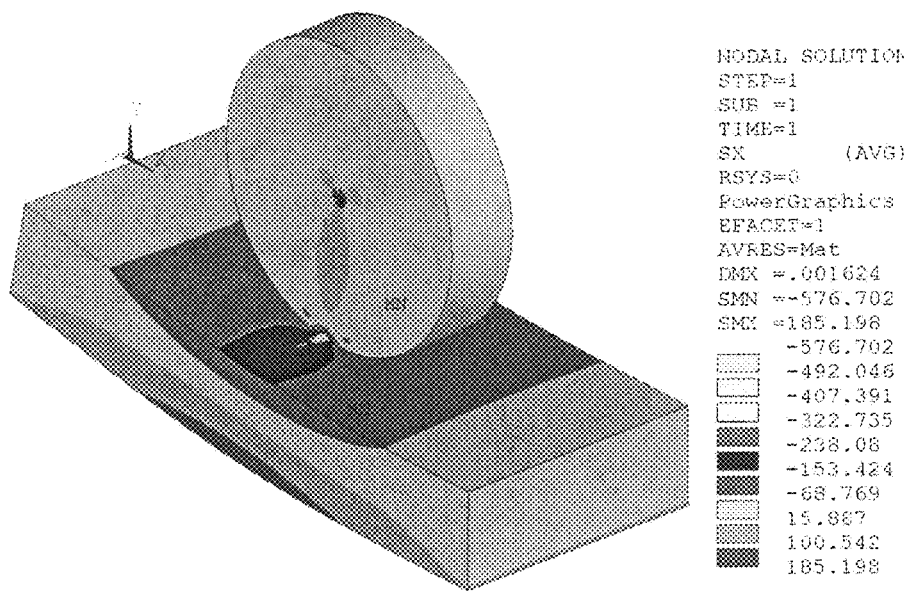
(b) Stress contour (unit: psi)
FIG. 10
The FEM model and stress distribution

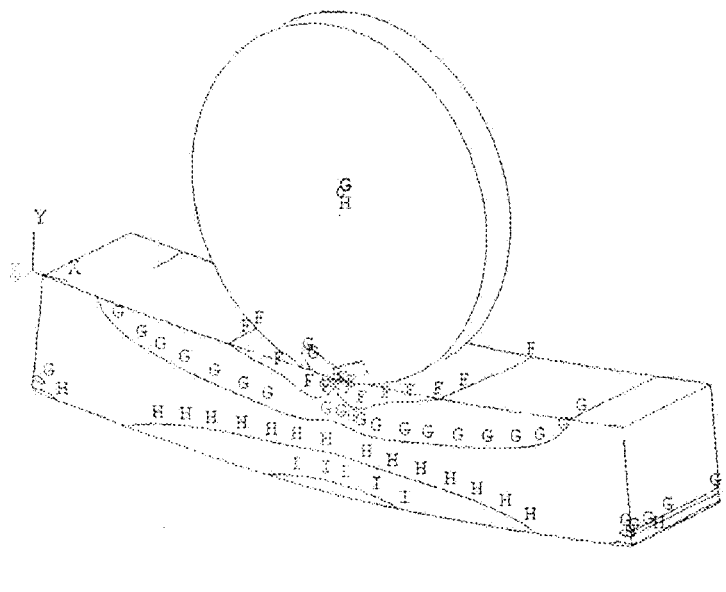
(a) Transverse section (along X-Y plane)
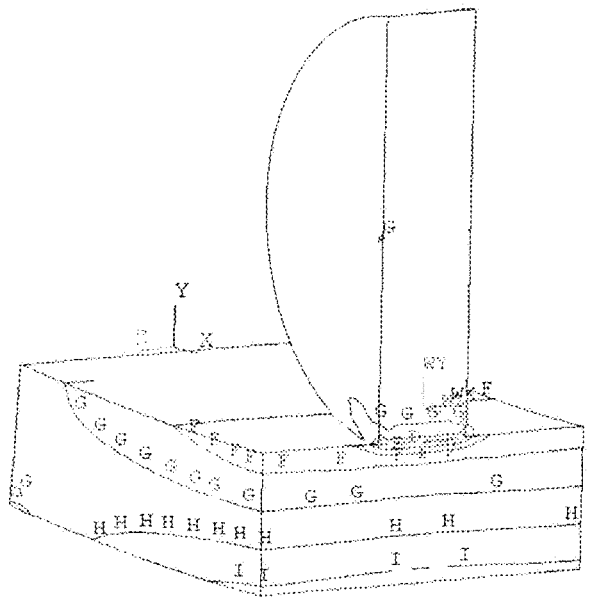
(b) longitudinal section (Y-Z plane)
FIG. 11
Graph of ISO-stress lines (unit: psi)

Normal stresses at the center of the bottom surface (3 cycles)

Typical sinusoidal stress induced by a loading wheel in APA (T=0.25s)

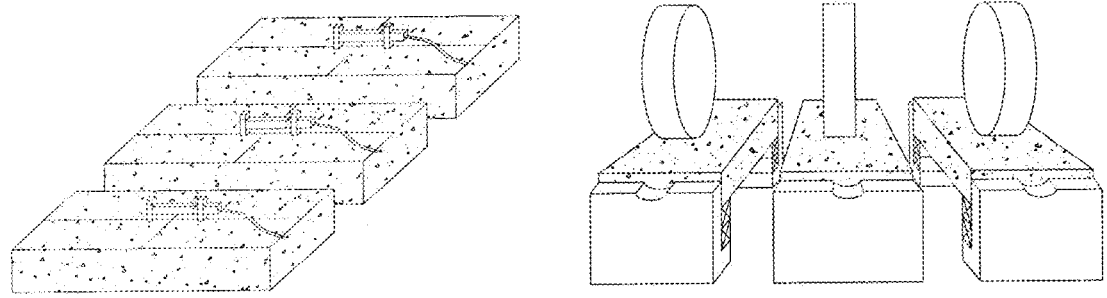
(a) Specimen with LVDT     (b) Movable wheel loading system
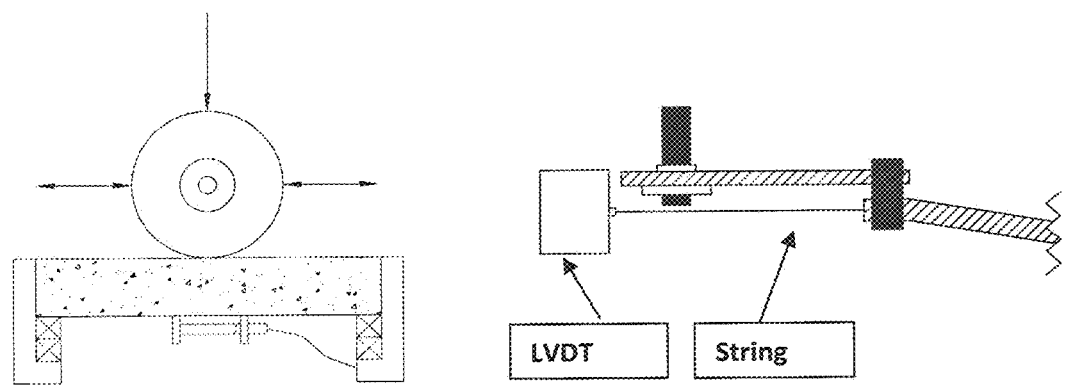
(c) Loaded wheel viscoelastic test setup     (d) Wheel movement measuring
FIG. 14
Loaded wheel viscoelastic property test

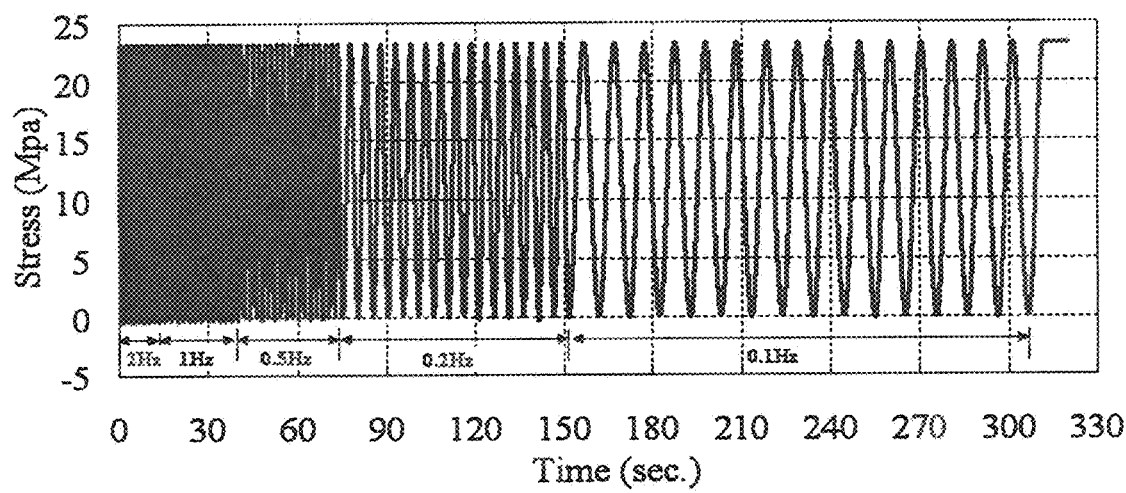
a) Sinusoidal stress
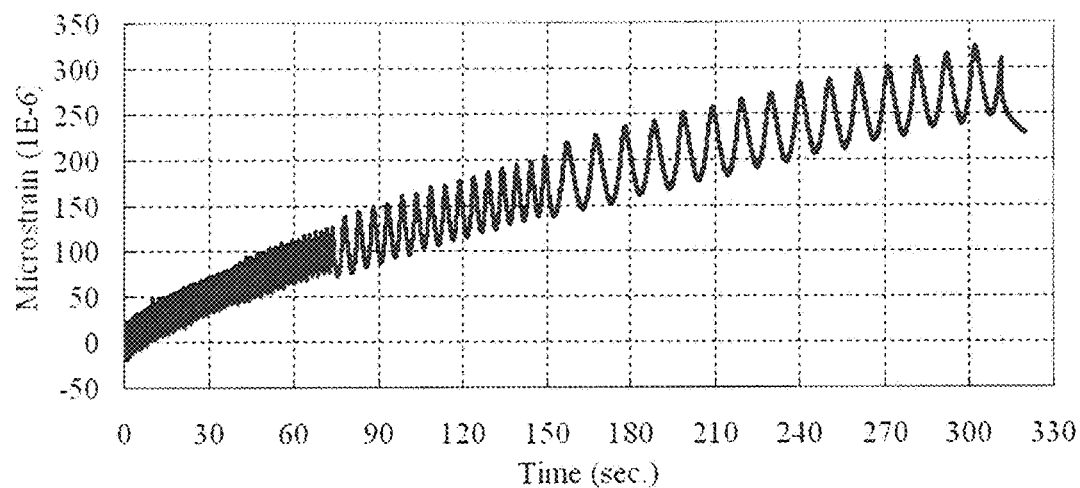
b) Measured tensile strain
FIG. 15
Typical stress and strain curves in a loaded wheel dynamic modulus test Typical hysteresis loops in a loaded wheel dynamic modulus test

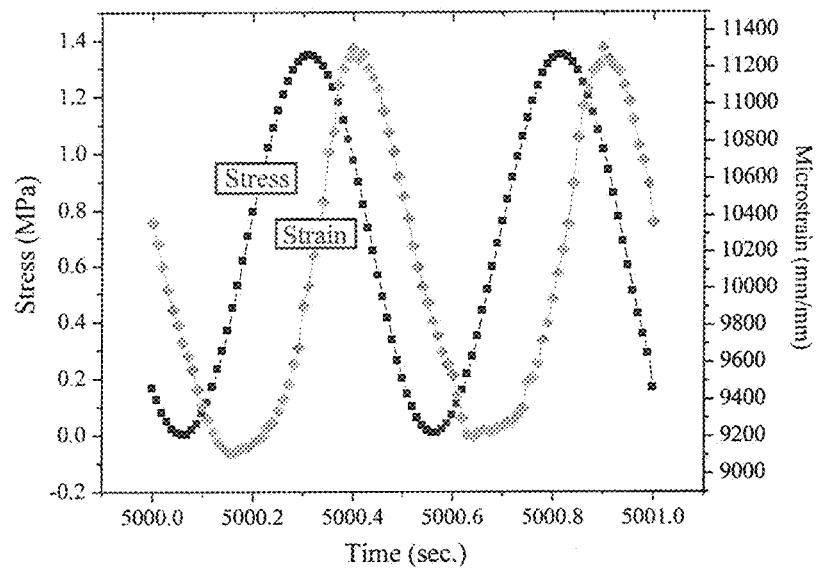
(a) Original data
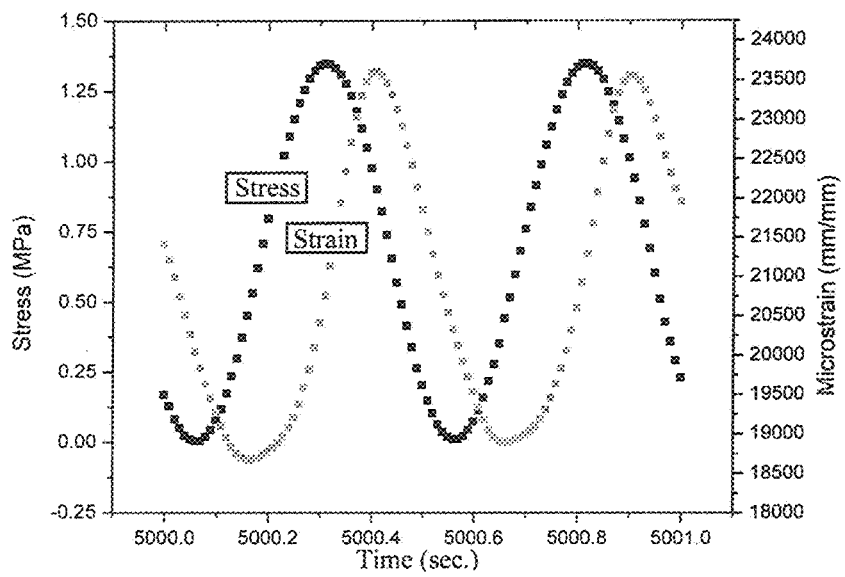
(b) FFT processed data
FIG. 17
Stress and strain curves before and after FFT smoothing process Creep compliance curves from a loaded wheel creep test (10°C)

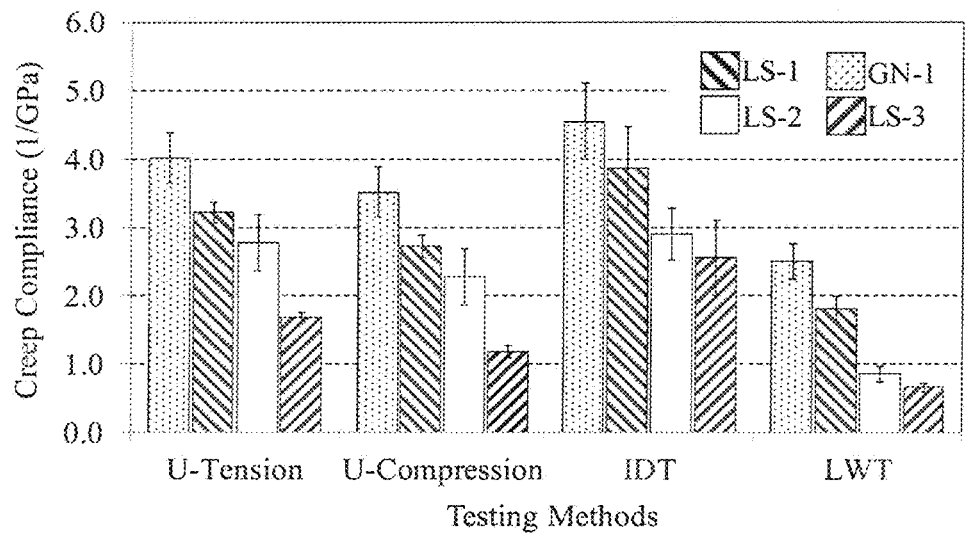
a) 10°C
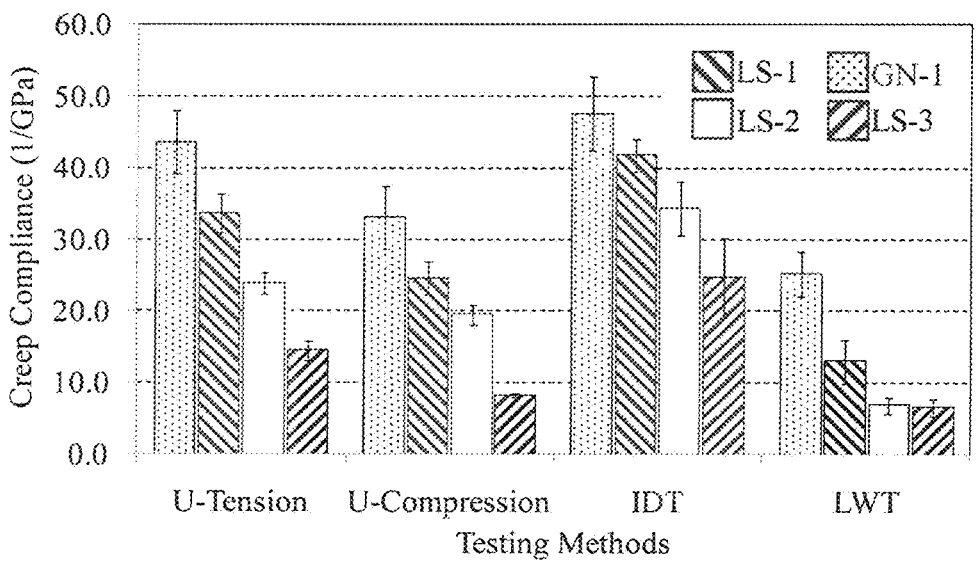
b) 25°C
FIG. 19
Creep compliances at 100s in different loading modes

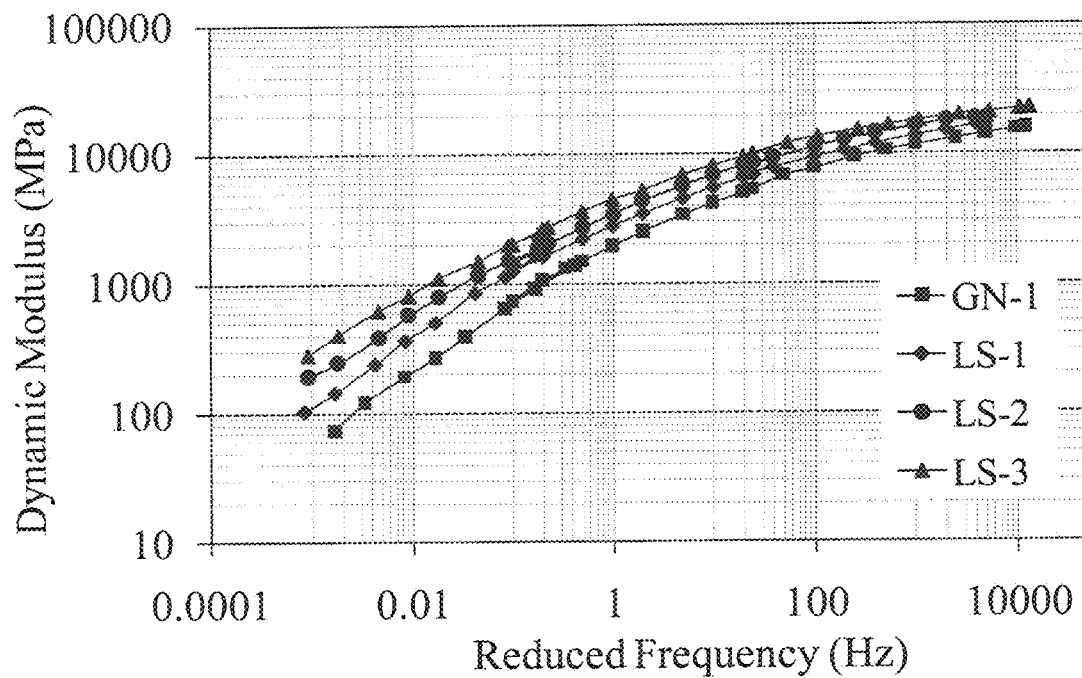
(a) Uniaxial tension
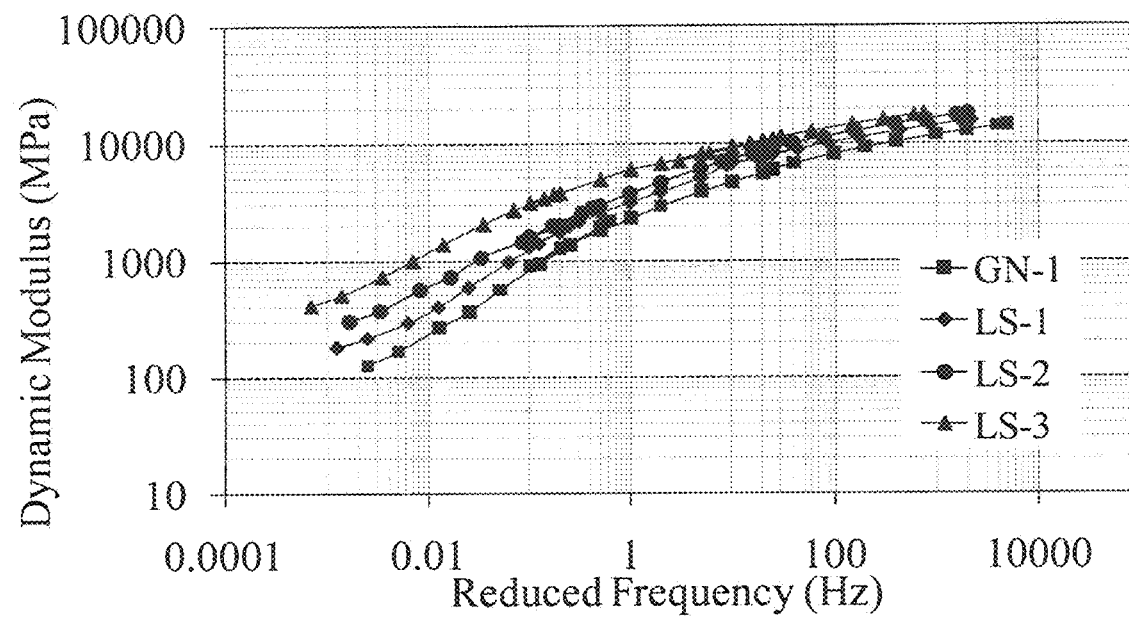
(b) Uniaxial tension-compression
FIG. 20
Dynamic modulus master curves from different tests

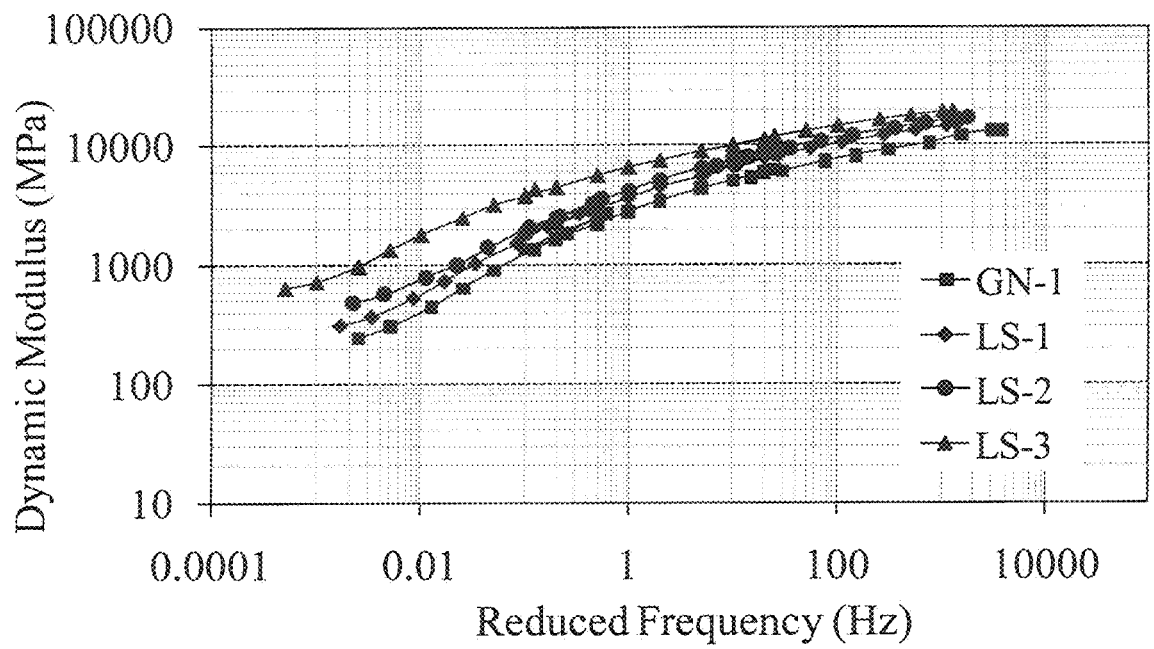
(c) Uniaxial compression
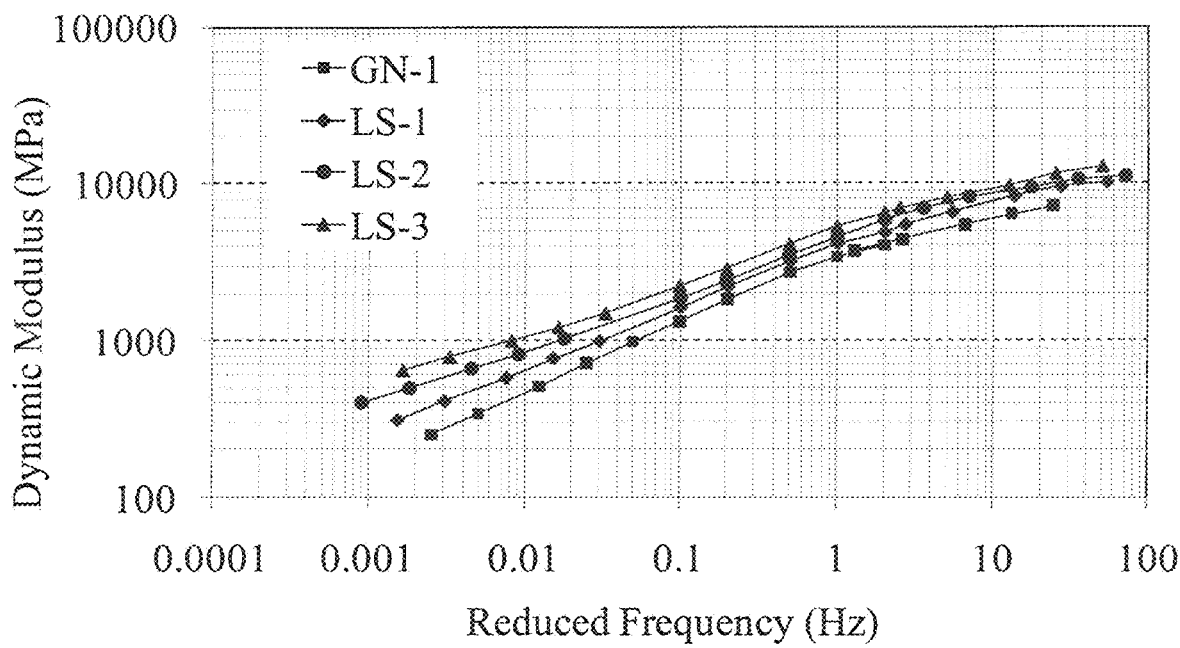
(d) Loaded wheel
FIG. 20 (cont.)
Dynamic modulus master curves from different tests Dynamic modulus master curves in different loading modes for asphalt mixture LS-3

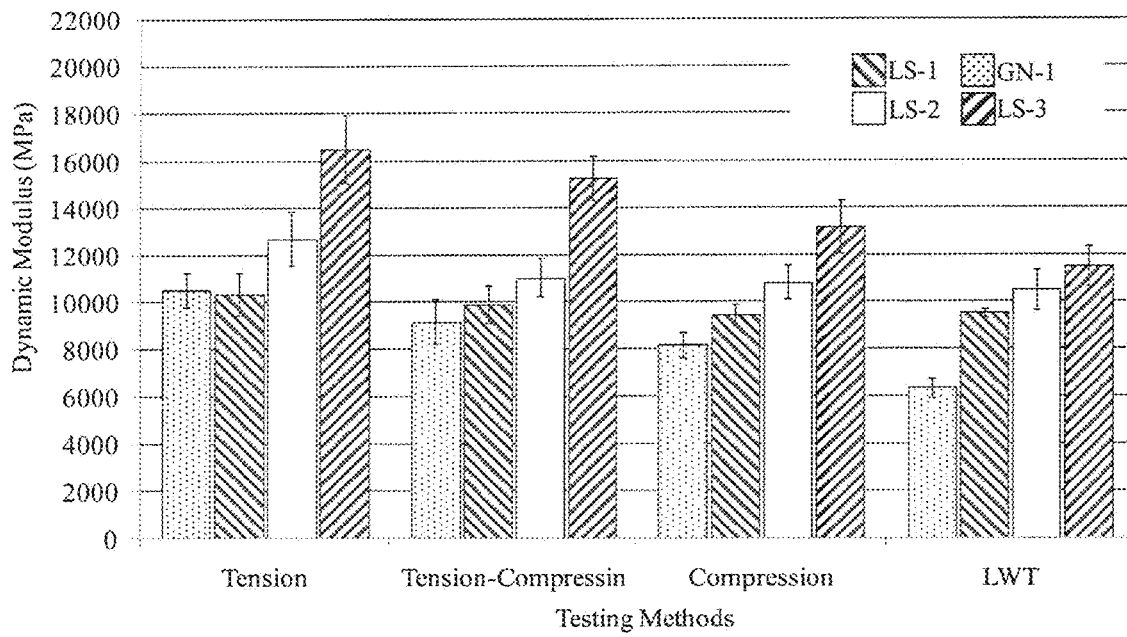
(a) 10°C, 2Hz
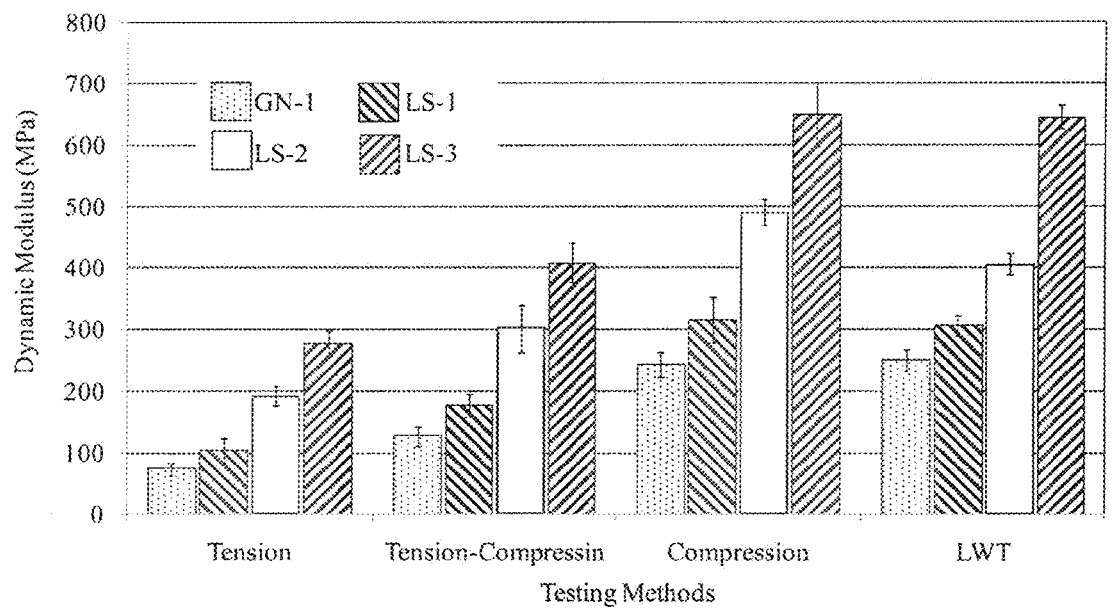
(b) 40°C, 0.01Hz
FIG. 22
Dynamic moduli at 10°C, 2Hz and 40°C, 0.1Hz

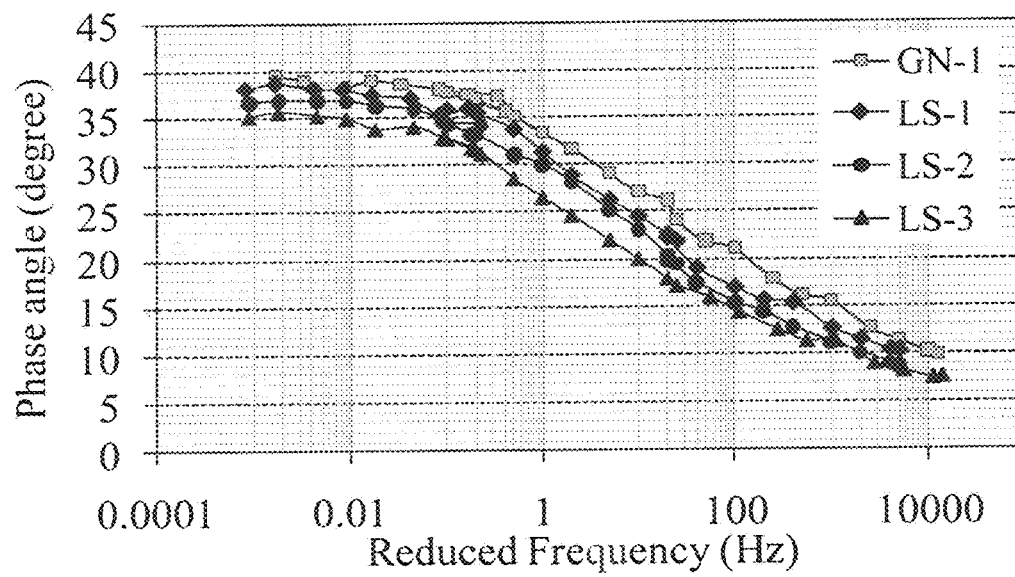
(a) Uniaxial tension
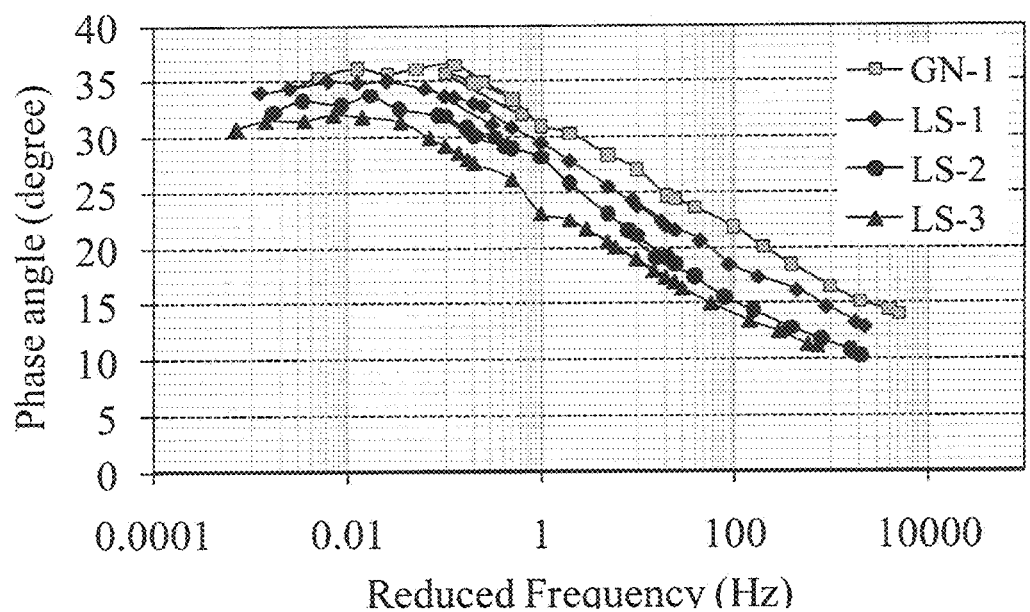
(b) Uniaxial tension-compression
FIG. 23 Phase angles from different tests

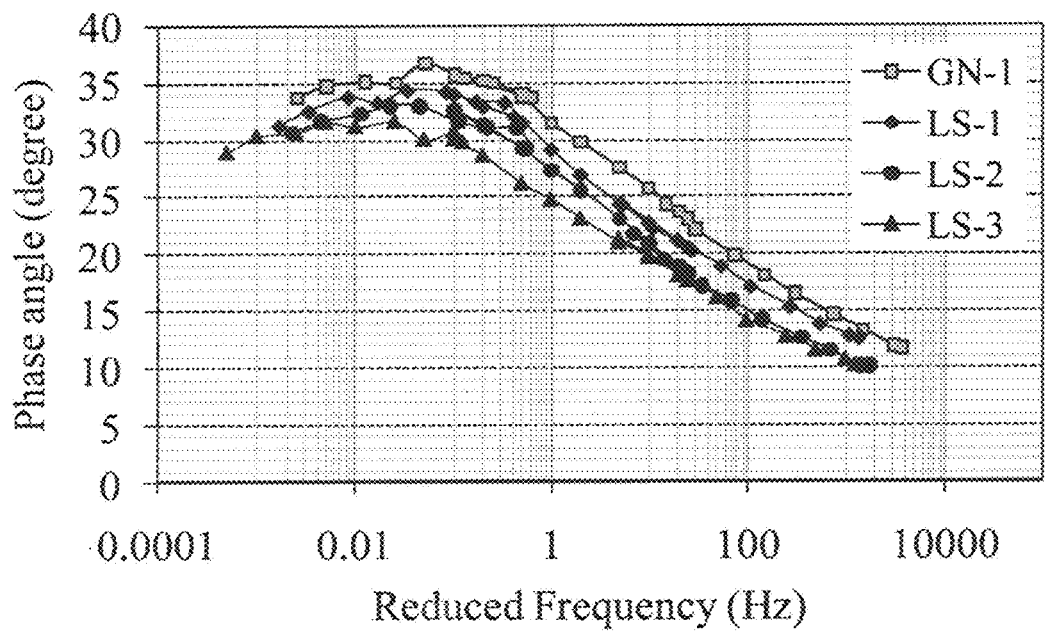
(c) Uniaxial compression
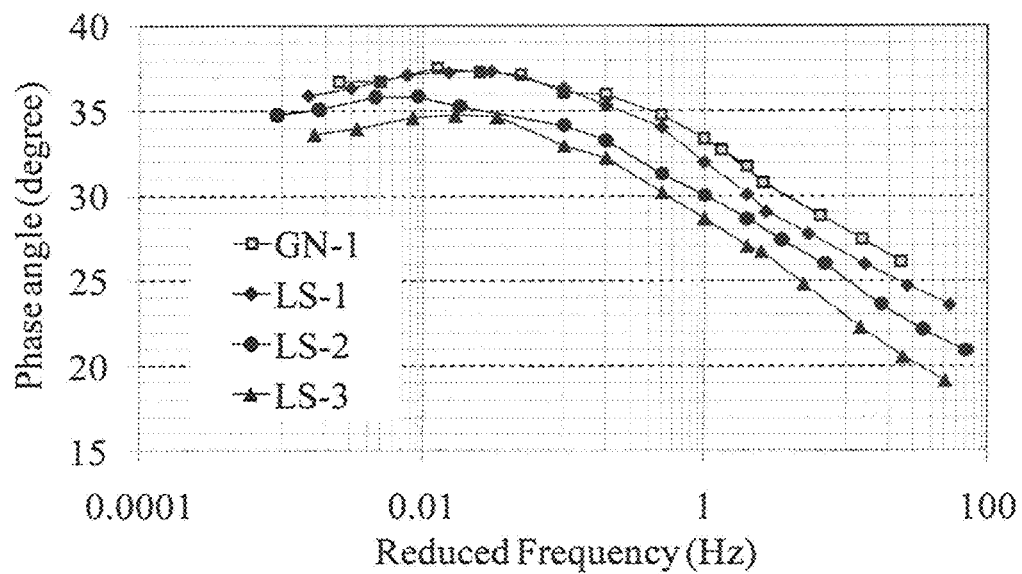
(d) LWT
FIG. 23 (cont.) Phase angles from different tests

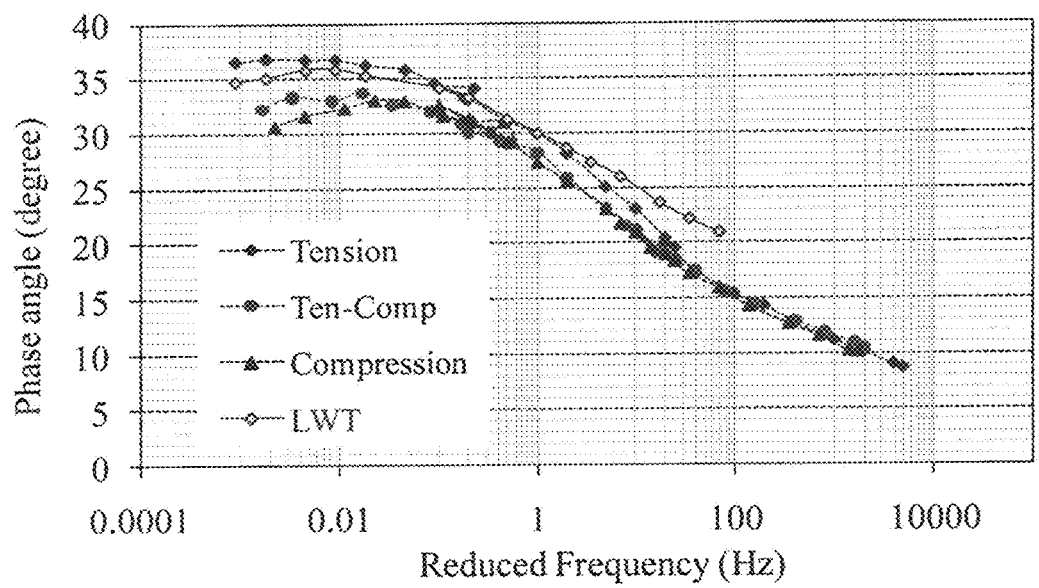
(a) LS-2
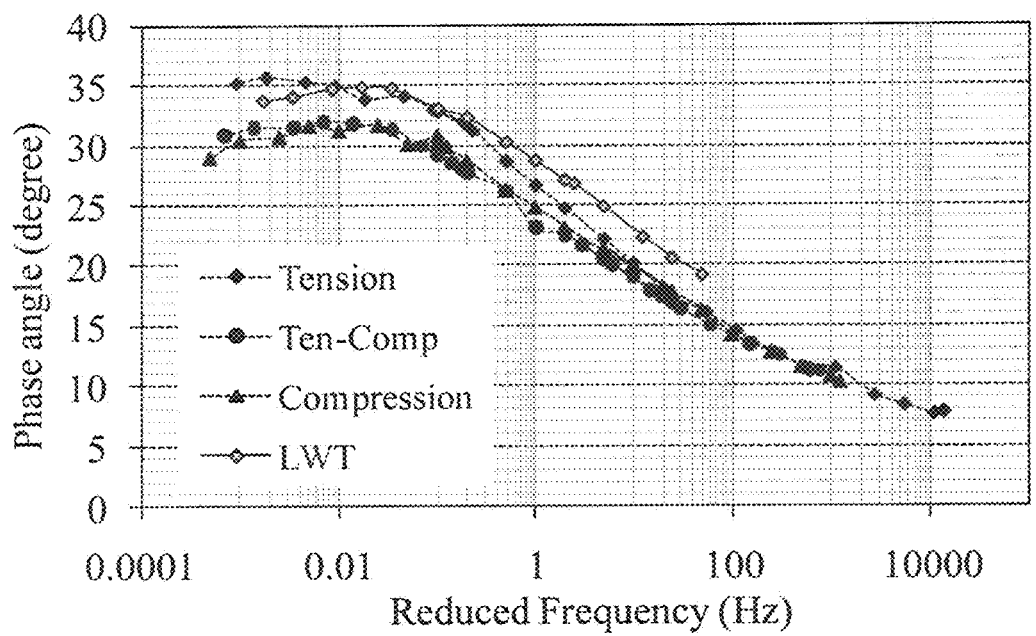
(b) LS-3
FIG. 24
Phase angles in various loading modes for asphalt mixtures LS-2 and LS-3

Typical developing phases in a fatigue test

Typical stress-strain hysteresis loop

Hysteresis loops at various cycles (from loaded wheel test)

Typical RDEC vs. load cycle curve (a) Direct tension (Prior Art) (b) Flexural beam (Prior Art) (c) Loaded wheel Sketch of the setups for three different fatigue tests

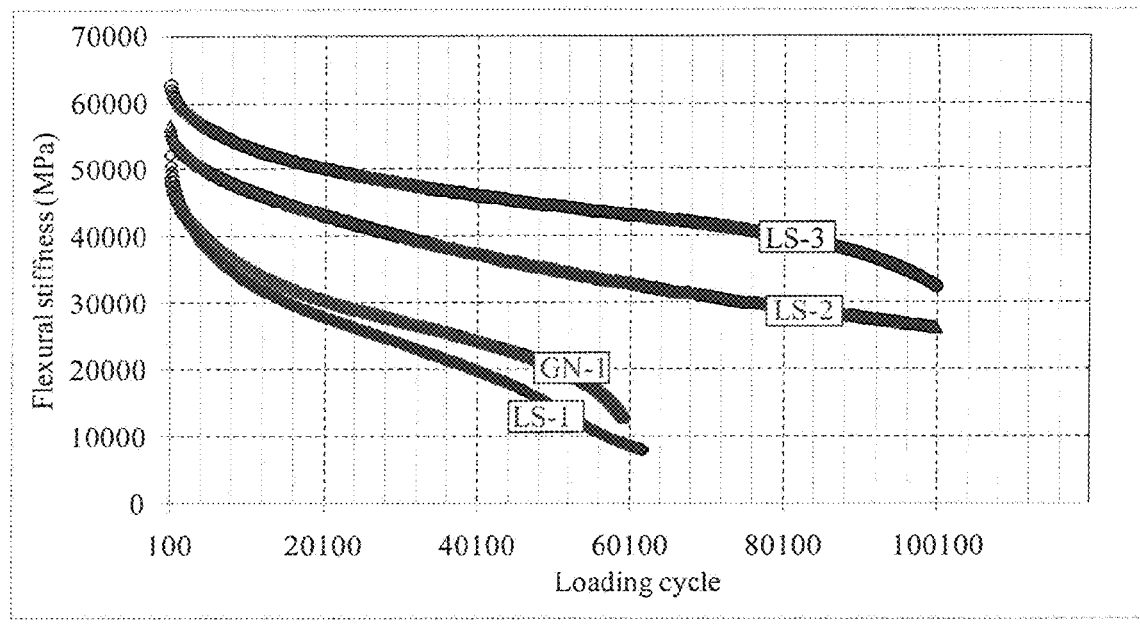
(a) Flexural beam fatigue test
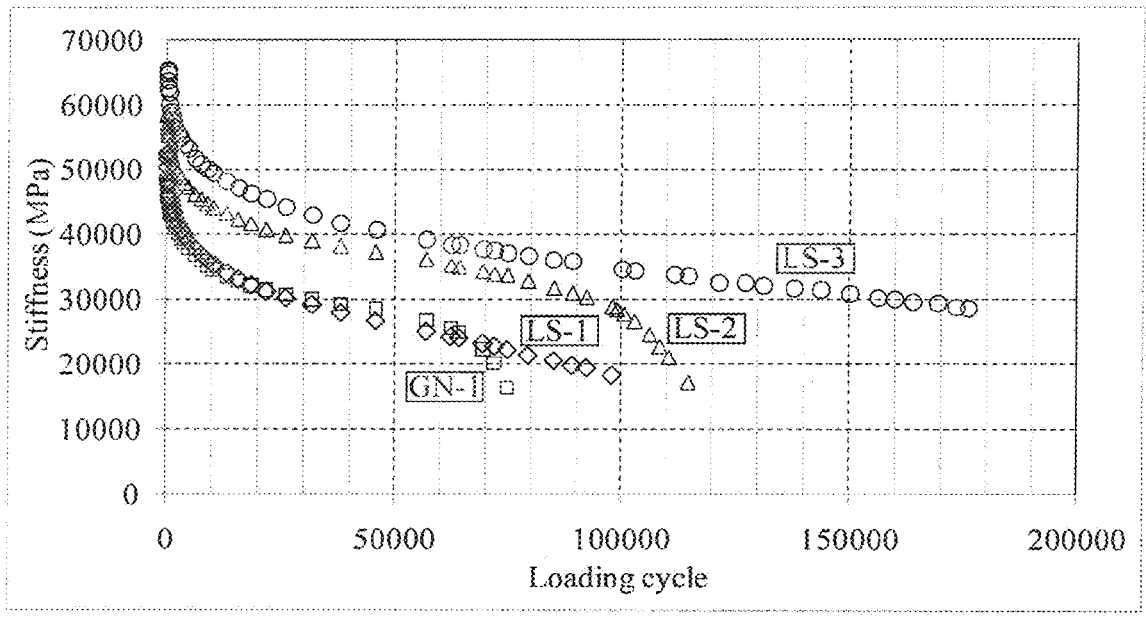
(b) Direct tension fatigue test
FIG. 30
Change of stiffness with increasing loading cycle in various tests (c) Loaded wheel fatigue test Change of stiffness with increasing loading cycle in various tests $N_f$ results from different fatigue tests for various mixtures Change of RDEC with increasing load cycle Plateau value results from different fatigue tests for various mixtures Relationship between PV and $N_f$

METHOD AND APPARATUS FOR FATIGUE AND VISCOELASTIC PROPERTY TESTING OF ASPHALT MIXTURES USING A LOADED WHEEL TESTER

This application claims the benefit of priority to U.S. Provisional Application Ser. No. 61/468,912, filed Mar. 29, 2011, of the same inventors and is incorporated by reference herein as to its entire contents.

BACKGROUND

1. Technical Field

The technical field relates to the testing of asphalt mixtures for the purposes, for example, of highway construction and, more particularly, to a method and apparatus for fatigue and viscoelastic property testing using a loaded wheel tester.

2. Description of the Related Arts

Loaded Wheel Testers (LWTs), such as the Asphalt Pavement Analyzer (APA) available from Pavement Technology, Inc. of Covington, Ga. (Pavement Technology), the Hamburg wheel tracking device, and the French LWT, are widely used in the United. States and many parts of the world to evaluate the rut-resistance and moisture susceptibility of asphalt mixtures. Referring to FIG. 1, there is shown the APA (Pavement Technology) testing process for fatigue properties of asphalt mixtures. The process involves using one or multiple loaded wheels to apply a moving load to specimens to simulate traffic loads applied on asphalt pavements. Based on the test results, the fatigue performance of asphalt mixtures can be evaluated.

An Asphalt Pavement Analyzer available from Pavement Technology has evolved over the years. At an early developmental stage of the Asphalt Pavement Analyzer (APA) and referring to FIG. 2(a), which is now one of the commonly used LWTs in the United States, the space under the beam specimen was small (indicated in black) and sometimes insufficient to accommodate the beam deformation caused by the moving wheel load during fatigue testing. At that time and referring to FIG. 2(b), conductive wires were attached to the bottom surface of the beam specimen with molten asphalt to detect the fatigue cracking of an asphalt beam test specimen. The fatigue is detected by the conductive wire breaking and demonstrating an open electric circuit. As the deformation at the bottom of the beam increased, the bottom surface of the sagging beam would come into contact with the rigid bottom plate and further vertical deformation would be stopped by the bottom plate; see FIG. 2(a). Under this situation, the conductive wires would not break, the final failure of the beam would be difficult to achieve or, if the conductive wire did break, the break in the wire might not be caused by fatigue cracking of the asphalt mixtures under test.

To enhance the simulation of fatigue cracking, the current version of the APA available from Pavement Technology has a deeper space under beam specimens, which can accommodate more deformation for beam specimens which depth is selected according to the length of the beam specimen under test; (see FIG. 1).

Moreover, viscoelastic testing was not provided for with an APA LWT. The viscoelastic properties of asphalt mixture have been the subject of many studies for several decades. A number of methods and analysis models, have been substantially developed to characterize the viscoelastic response of asphalt mixtures as well. Viscoelasticity as used herein may be defined, for example, as the property of an asphalt mixture to exhibit both viscous and elastic characteristics when undergoing vehicular traffic and environmental phenomenon but this definition is not intended to be limited herein. Due to the inherent nature of viscoelastic materials, the fundamental property that governs the responses caused by external loading is a function of time or loading frequency. Linear viscoelastic behavior for asphalt mixtures may be determined through experimental testing within the linear viscoelastic region, such as creep, relaxation, and complex modulus tests. Due to the challenge of controlling a relaxation test, a creep test is more accepted by researchers based on the interchangeability of the results from both tests. The creep test involves measuring the time dependent strain (e.g. deformation) induced from the application of a constant uniaxial stress, $\sigma_0$. Creep compliance is defined as the ratio of the time-dependent strain to the constant stress. The creep compliance is a crucial factor for determining the suitability of asphalt concrete under various loading and environmental conditions. Moreover, once the creep compliance is determined, the stress-stain relationship can be expressed with hereditary integral $$\varepsilon(t) = \sigma_i J(t) + \int_0^t J(t-t') \frac{\partial \sigma'}{\partial t'} dt' \quad (1.1)$$

where, $\varepsilon(t)$=strain; $\sigma_t$=initial stress; t'=integration variable related to time.

The complex modulus test is a fundamental test that characterizes the viscoelastic properties of asphalt mixtures. It is considered as a mechanistically based laboratory test to characterize the stiffness and loading resistance of asphalt mixtures. Complex modulus, E*, is composed of real and imaginary parts that define the elastic and viscous behavior for viscoelastic materials. Dynamic modulus, |E*|, obtained from the test is a fundamental property for describing the stress-strain relationship of asphalt mixtures, while phase angle, $\delta$, is a major factor reflecting the viscous behavior of asphalt mixtures which indicates whether the asphalt material is predominantly elastic or viscous.

$$E^* = \frac{\sigma_{amp} e^{i\omega t}}{\varepsilon_{amp} e^{i(\omega t - \delta)}} \quad (1.2)$$

$$|E^*| = \frac{\sigma_{amp}}{\varepsilon_{amp}} \quad (1.3)$$

$$\delta = 2\pi \cdot f \cdot \Delta t \quad (1.4)$$

where, $\sigma_{amp}$=amplitude of sinusoidal stress; $\varepsilon_{amp}$=amplitude of sinusoidal strain; $\omega$=angular velocity; i=imaginary component; f=loading frequency; $\Delta t$=time lag between stress and strain.

Dynamic modulus values measured over a range of temperatures and frequencies of loading can be shifted into a master curve based on a time-temperature superposition principle. The master curve of an asphalt mixture allows comparisons to be made over extended ranges of frequencies and temperature, so that dynamic modulus can be used as an important viscoelastic parameter for performance analysis of asphalt mixtures using constitutive models. Besides, dynamic modulus is also a crucial parameter for pavement design. Most of the researches indicate that any process that results in the use of asphalt mixtures with better selection of dynamic modulus will improve the performance of the pavement.

Although many factors have been proved to have significant effects on the viscoelastic behavior of asphalt material, such as loading magnitude, rate of loading (loading frequency), and temperature variations, there are only a few direct evidences or relative works regarding evaluation of the effect of the loading mode (e.g. tension, tension/compression and compression). Through testing loading conditions different from the actual states, significant errors and unreasonable design may occur. Currently, several testing methods and devices have been created to investigate the viscoelastic properties of asphalt concrete based on creep and complex modulus tests in all kinds of testing situations. According to the fundamental stress and strain situation in the asphalt pavement, the fatigue life of a particular asphalt pavement mixture is primarily determined by the tensile properties of the asphalt mixture it comprises. Therefore, it is more appropriate to use the parameters obtained from a tension test to evaluate the performance of asphalt concrete. In fact, a pavement structure is subjected to a triaxial stress state under actual vehicular traffic loading. As a continuous medium, pavement structure tends to spread the stress out received from the vehicular traffic in all directions. With the development of better testing equipment and analysis methods, it becomes possible to better simulate the stress state of pavement structure in laboratory testing. Although all kinds of stress states such as uniaxial, biaxial, and triaxial can be simulated in the laboratory, the real stress state that exists in the pavement cannot be achieved. The development of testing method is still the bottleneck for achieving a better and clearer understanding of pavement material properties.

For testing viscoelastic properties, three known tests are shown in FIGS. 5(a), (b) and (c). These include the Direct Tension Test (DTT) for testing asphalt concrete in tension depicted in FIG. 5(a). A unique benefit of the DTT test is that the stress of the specimen is in a uniaxial tension state which makes the stress-strain analysis much simpler. The Simple Performance Test depicted in FIG. 5(b), also known as the asphalt mixture performance test (AMPT), tests a cylindrical specimen for controlled sinusoidal stress loading at various loading frequencies and test temperatures. An indirect tension (IDT) testing method, depicted in FIG. 5(c), characterizes Poisson's ratio, creep compliance, resilient modulus and splitting tensile strength of asphalt mixtures by subjecting the depicted cylindrical specimen to a diametrical load.

Consequently, there is an opportunity to improve test apparatus and a method for asphalt mixtures using a loaded wheel tester or related apparatus.

SUMMARY

Referring to FIG. 3, a test specimen may be adapted to provide additional output. For example, a linear variable differential transformer (LVDT) or other strain determining device may be mounted at the middle of the bottom surface of a beam specimen, e.g. in a length-wise direction, to accurately measure the deformation information of the specimen under the reciprocating wheel load.

The loaded wheel tester (LWT) fatigue test was compared with two other asphalt mixture fatigue tests, the flexural beam fatigue test and the uniaxial direct tension fatigue test. Table 1 presents the testing conditions of the three fatigue tests. Table 2 presents the information about the four asphalt mixtures used in the experiments. Table 3 presents the information about the test specimens for the three different fatigue tests.

TABLE 1

Three Fatigue Tests

| Fatigue Test | Test Temperature | Loading Frequency | Strain/Stress Level | Test Equipment |
|---|---|---|---|---|
| Flexural Beam | 10° C. | 10 Hz | 500 µε | Beam Fatigue Apparatus (BFA) |
| Uniaxial Direct Tension | 10° C. | 2 Hz | 382 kPa | Material Testing System (MTS) |
| Loaded Wheel | 10° C. | 2 Hz | 1132 kPa | Asphalt Pavement Analyzer (APA) |

TABLE 2

Four Asphalt Mixture Used in Fatigue Testing

| Mixture ID | Aggregate | Asphalt Binder | Asphalt Binder Content |
|---|---|---|---|
| GN-1 | Granite | PG 64-22 | 5.8% |
| LS-1 | Limestone | PG 64-22 | 5.0% |
| LS-2 | Limestone | PG 70-22 | 5.0% |
| LS-3 | Limestone | PG 76-22 | 5.0% |

TABLE 3

Asphalt Mixture Specimens for Fatigue Testing

| Fatigue Test | Specimen Type | Compaction Method | Air Voids (%) |
|---|---|---|---|
| Flexural Beam | Beam: 380 mm × 50 mm × 63 mm | Asphalt Vibratory Compactor (AVC) | 4 ± 1 |
| Uniaxial Direct Tension | Cylinder: 100-mm diameter and 150-mm height | Superpave Gyratory Compactor (SGC) | 4 ± 1 |
| Loaded Wheel | Beam: 300 mm × 125 mm × 50 mm | Asphalt Vibratory Compactor (AVC) | 5 ± 1 |

In the analysis of the fatigue test results, two analysis methods were used. One is the conventional 50% reduction in initial stiffness and the other the plateau value method. In the 50% stiffness reduction method, the fatigue life ($N_f$) is defined as the number of loading cycles the specimen has undergone when the flexural stiffness reaches 50% of its initial value. In the plateau value method, a new term, ratio of dissipated energy change (RDEC), is defined as a ratio of the change in dissipated energy between two neighboring cycles to the dissipated energy in the first of the two neighboring cycles. A plateau value (PV), or the nearly constant value of RDEC, can be determined. The lower the PV, the longer the fatigue life for a specific asphalt mixture. Referring to FIG. 4, there is shown a comparison of the results from the three fatigue tests where a loaded wheel test according to an embodiment of the invention has been briefly described above. It may become clear that the results from the three fatigue tests on the four different asphalt mixtures tested agree very well, indicating that an LWT fatigue test and apparatus modified as suggested above may produce very consistent and comparable results with known, more complex tests and associated apparatus.

Referring briefly to FIG. 5(d), a test process for viscoelastic properties employing an LWT and, for example, a test specimen, for example, having a linear variable displacement transducer (LVDT) mounted thereon is depicted side-by-side with the known DTT, SPT and IDT test methods. As will be discussed further herein in particular detail, an LWT test as so modified provides favorable comparative test results to known tests including evaluation of phase angle.

Embodiments of test apparatus and methods for fatigue and viscoelastic property testing using a loaded wheel tester will now be described with reference to the drawings, a brief description thereof provided below followed by a detailed description thereof.

BRIEF DESCRIPTION OF THE DRAWINGS

FIG. 3 shows how a test specimen may be adapted to provide additional output for, for example, testing for viscoelastic and fatigue properties.

FIG. 4 shows a comparison of results from three fatigue tests including results from use of an LWT modified according to an embodiment.

FIGS. 5(a), 5(b) and 5(c) shows three known tests for viscoelastic properties; FIG. 5(d) shows one using an LWT according to an embodiment; FIG. 5(e) shows a simplified block schematic diagram of a modified loaded wheel tester according to an embodiment.

FIG. 6 shows a schematic diagram of a modified APA loading system.

FIG. 10 shows the finite element method (FEM) model and stress distribution.

FIG. 11 shows a graph of ISO-stress lines (unit: psi).

FIG. 14 shows a loaded wheel viscoelastic property test.

FIG. 15 shows typical stress and strain curves in a loaded wheel dynamic modulus test.

FIG. 17 shows stress and strain curves before (FIG. 17(a)) and after (FIG. 17(b)) a fast Fourier transform (FFT) smoothing process, (strain lagging stress in both curves).

FIG. 19 shows creep compliances at 100 seconds in different loading modes.

FIG. 20 shows dynamic modulus master curves from different tests.

FIG. 22 shows dynamic moduli at 10° C., 2 Hz and 40° C., 0.1 Hz.

FIG. 23 shows phase angles from different tests.

FIG. 24 shows phase angles in various loading modes for asphalt mixtures LS-2 and LS-3.

DETAILED DESCRIPTION

Viscoelastic Property Testing

With reference to FIGS. 5(d)-24, an approach to testing viscoelastic properties of, for example, asphalt mixtures will be discussed. The viscoelastic property test using a modified LWT will be discussed for (a) characterizing the viscoelastic properties of asphalt mixtures; (b) estimating the feasibility of using an LWT viscoelastic property test to differentiate the viscoelastic properties of different asphalt mixtures; and (c) meanwhile, conducting known indirect tension (IDT) test and uniaxial tests in three different loading modes (e.g. tension, tension/compression and compression) as parallel tests to compare to LWT viscoelastic tests using modified known APA apparatus.

Two different types of aggregates, limestone and granite, were considered. Three grades of asphalt binder, PG 64-22, PG 70-22 and PG 76-22 were used for the mixtures made with limestone aggregate, while PG 64-22 asphalt binder was used for the mixtures made with granite aggregate.

Movement Equation and Simplified Mechanical Model

Figure 1:
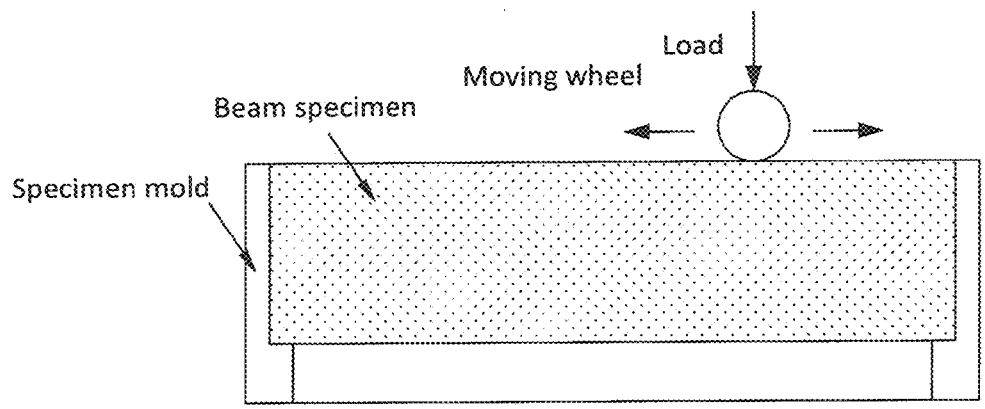
FIG. 1 shows a known APA (Pavement Technology) testing process for fatigue properties of asphalt mixtures.
Figure 2:
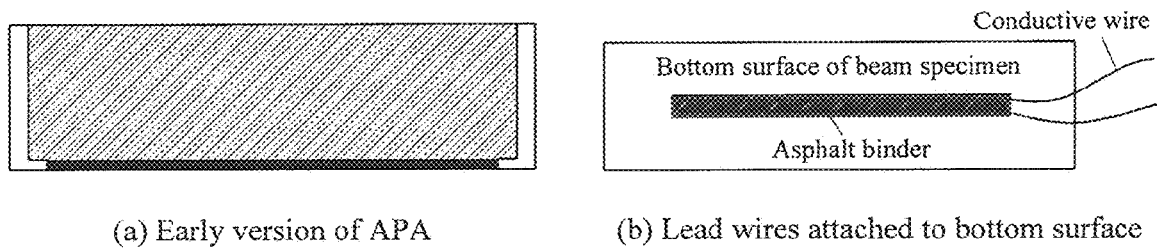
FIG. 2 shows an early version of APA for fatigue testing.
Figure 7:
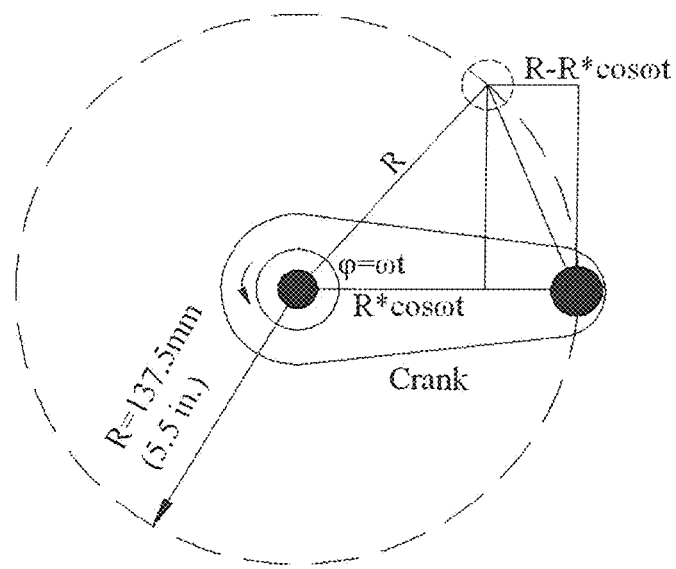
FIG. 7 shows establishment of a movement equation.
Figure 8:
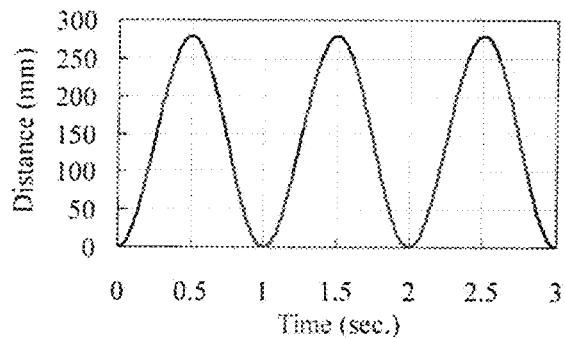
FIG. 8 shows a movement function of a modified APA loading system (Tr=1).
Figure 9:
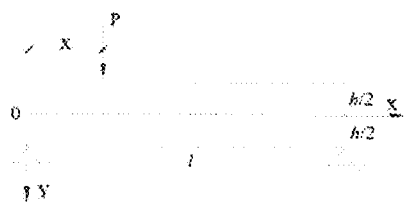
FIG. 9 shows a simplified mechanical model for stress analysis.

FIGS. 5(d), 5(e), 6 and 7 provide mechanical and electrical schematic diagrams for a loaded wheel tester model while FIG. 8 provides an exemplary wheel movement function showing distance versus time for movement of a loaded wheel. For an APA system as modified per FIG. 6, the velocity of the loading wheels or the frequency of the cyclic loading can be adjusted by specifying the angular frequency of the depicted axis of rotation. The axis of rotation drives the crank to do a circular motion, so that the'transmission shaft (FIG. 6(b)) will be forced to move back and forth with the loading wheels attached to connecting rods. A linear variable differential transformer (not shown in FIG. 6) may be connected between a stationary frame of the apparatus and the moving loaded wheel to accurately determine wheel location at a given point in time. The apparatus may be deployed within an environmental chamber (not shown) for control of temperature and other environmental variables.

FIG. 5(e) shows a simplified block schematic diagram of a modified loaded wheel tester 500 according to an embodiment. An LWT 510, for example, shown in FIGS. 5(d), 6, 7, 14(d) and 29(d) may be placed in an environmental chamber 520. The LWT 510 comprises sensors, for example, linear variable differential transformers discussed herein, for determining stress/strain and location, angular velocity sensors for determining actual angular velocity of axis of rotation (FIG. 6), humidity sensors, temperature sensors (for example, within a specimen under test or within environmental chamber 520) and the like that may be provided for performing viscoelastic property and fatigue testing as discussed herein. An input device 570 may be used to input selections of temperature, test durations, test waiting intervals, loading cycles per second and other input information for LWT 510 as well as to control operation of data processor 540 to perform a given calculation or output a requested graph on output device 550. An input device may be any such device including a keyboard, a mouse for clicking with a graphical user interface or touch screen or other known input device. Data acquisition system 530 acquires data from all sensors and may output the data obtained for temporary or permanent storage in memory 560 such as loading cycles per second for each loaded wheel, temperature in the test specimen, temperature in the environmental chamber 520, stress or strain as determined by gauges such as via LVDT's and location of a loaded wheel via, for example, an LVDT and string per FIG. 14(*d*). Input device 570 may control the environment within environmental chamber 520 by, for example, regulating temperature, humidity and atmospheric pressure as selected or input by a user as well as the operation of a motor of LWT 510 at a selected or input angular velocity and resultant sinusoidal movement of its loaded wheels. Data processor 540 may be a data processor known in the art for performing mathematical analysis of acquired data according to the several equations discussed herein in coordination with the data acquisition system 530 and memory 560. A clock is not shown but is assumed with any data processor 540 for measuring seconds or minutes of time. Moreover, a counter may be assumed for any data processor 540 for counting loaded wheel cycles and comparison, for example, with fatigue values to determine cycles or time to fatigue of a given test sample. Data processor 540 may operate under control of computer programs which may be local or run remotely through the internet cloud. Data processor 540 computes, stores in memory 560 and may display, for example, a master curve of dynamic moduli for a given test sample measured at a given frequency and a given temperature and may, for example, output data to a display for comparing test samples to determine one asphalt mixture sample that may perform better than another different mixture. Output device 550 then may comprise a display, a printer or any other output device known in the art and output data may be communicated remotely via a communications interface not shown. Data processor 540 in combination with output device 550 may thus transform raw data into a graphical or other form that may be useful to determine a particular asphalt mixture for a particular application, for example, as a road surface choice in a given climate in a given geographical area, such as Tennessee, USA. As one of ordinary skill reads the description of viscoelastic property measurement and fatigue testing using a modified LWT 510 one will appreciate the utility of system 500 and may utilize the suggested size relationship between test specimens and loaded wheels and the compacting techniques discussed herein to form the specimens and achieve the results desired.

In terms of the motion of the system (FIG. 7), the movement equation for the loading wheels can be expressed as the following formula:

$$S = R \cdot (1 - \cos\omega t), \quad \omega = \frac{2\pi}{T_r} \tag{1.5}$$

where, S=distance of movement of the wheels; R=radius of the rotation of crank (also equals to ½ path length of the loading wheels); ω=angular frequency of the rotation axis; $T_r$=rotation period of the circular motion of crank.

Based on the motion equation above, a loading process of the moveable wheels can be regarded as a simple harmonic motion and displayed. (e.g., FIG. 8 for a one second period), and the mechanical model can be simplified as per the mechanical model of FIG. 9.

For the beam sample subjected to a continuous sinusoidal load, the distribution of the stress along the bottom surface of a beam specimen can be expressed as the formula below with respect to wheel travel distance and time.

$$\begin{cases} \sigma(x, t) = \dfrac{3P \cdot \sin^2\left(\dfrac{2\pi}{T} \cdot t\right) \cdot x}{bh^2}, & x \leq \dfrac{l}{2} \\ \sigma(x, t) = \dfrac{3P \cdot \sin^2\left(\dfrac{2\pi}{T} \cdot t\right) \cdot (l-x)}{bh^2}, & \dfrac{l}{2} < x \leq l \end{cases} \tag{1.6}$$

where, P=wheel loading; l=length of the loading path; b=width of specimen; h=height of specimen; T=testing period; t=elapsed testing time.

Stress Analysis

Based on the analysis above, the system could be simplified as a simple supported beam subjected to a moving load. According to the theory of mechanics, the error caused by the assumption of plane-stress could be negligible if the width of the wheel equals to the width of the beam specimen. However, the width of the wheel in the loading system is only about ⅓ of the width of the beam specimen. In order to appraise the error caused by the simplification from a 3-Dimension (3-D) problem to a 2-Dimension (2-D) plane-stress problem, the Finite Element Method (FEM) was used to calculate the stress of the beam specimen. The FEM model and stress distribution are shown in FIG. 10. The element mesh of the wheel loading path area has been refined to improve the calculation accuracy.

During the calculation, vertical nodal forces may be placed on the central axis of the wheel to simulate the wheel load (e.g., determined via actuator and pressure transducer of FIG. 6(*b*)). FIG. 10 also shows the stress contour when the beam specimen is subjected to a wheel load at the middle. Furthermore, the ISO-stress lines of the beam specimen under the wheel load are illustrated in FIG. 11, the wheel load used for this calculation is 889 N (200 lb), and the unit of the stresses presented in the graph is psi.

In the case shown above, the maximum tensile stress was on the bottom surface of a beam specimen under test and at the middle of the beam. In FIG. 10, the value of the maximum tensile stress was 1.28 MPa (185.2 psi) from the 3-D FEM calculation, while it was 1.24 MPa (180.0 psi) from the calculation of 2-D beam. Hence, the error of the amplitude of the sinusoidal tensile stress was only about 3% due to a simplification from a 3-D to a 2-D problem, which is usually within the engineering tolerance.

Figure 12:
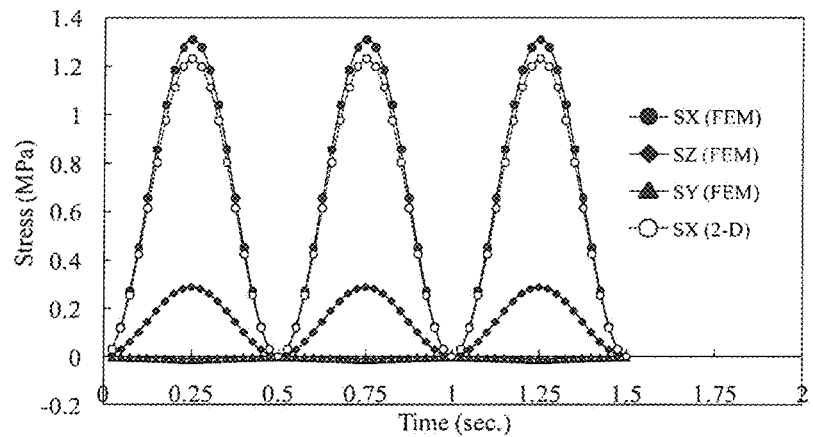
FIG. 12 shows normal stresses at the center of the bottom surface of a test specimen (3 cycles).

The three normal stresses at the middle of the bottom surface of a beam specimen under test within three loading cycles are shown in FIG. 12. The major stress the beam is subjected to is the normal stress in x direction (longitudinal direction), SX, which is more than four times the normal stress in z direction (transverse direction), SZ. In comparison to SX and SZ, the stress in y direction (vertical direction), SY, is negligible. Besides, it is obvious that only small errors exist between the results from the 3-D FEM and 2-D plane stress calculations.

Viscoelastic Property Testing

1. Dynamic Modulus Test

Figure 13:
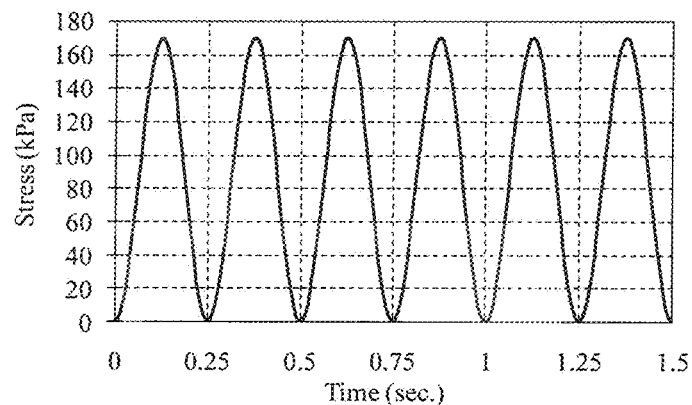
FIG. 13 shows a typical sinusoidal stress induced by loading wheel in a modified APA (T=0.25 s).

Dynamic modulus testing could be conducted by the modified APA system, since loading frequency is able to be controlled. Continuous sinusoidal loading applied by the modified APA loading system will induce a sinusoidal strain with a time lag related to phase angle. The relationship between tensile stress, $\sigma_0$, at the middle of the bottom surface of the beam specimen and the elapsed-time of cyclic loading can be obtained as:

$$\sigma_0 = \sigma_{amp} \cdot \sin^2\left(\frac{2\pi}{T} \cdot t\right) \quad (1.7)$$

where, $\sigma_{amp}$=amplitude of sinusoidal stress; T=testing period (cycle/sec.). Because one cycle of the loading wheels from one end of the beam sample to the other end leads to two identical cycles for tensile stress, so the actual loading frequency of sinusoidal stress is twice the frequency of the movement of the loading wheels (T=$T_r$/2). The typical sinusoidal stress induced by the APA loading wheels is shown in FIG. 13.

Thus, the dynamic modulus can be calculated as:

$$|E^*| = \frac{\sigma_{amp}}{\varepsilon_{amp}} = \frac{3l \cdot P}{2bh^2 \cdot \varepsilon_{amp}} \quad (1.8)$$

where, $\sigma_{amp}$=amplitude of sinusoidal stress; $\epsilon_{amp}$=amplitude of measured strain. And the phase angle can be obtained as:

$$\delta = 2\pi \cdot f \cdot \Delta t \quad (1.9)$$

where, f=loading frequency; $\Delta t$=time lag between stress and strain.

2. Creep Test

When a constant load is applied at the middle of the beam specimen under test, the stress induced on the bottom surface is:

$$\sigma_0 = \frac{3Pl}{2bh^2}.$$

Thus, the creep compliance can be expressed as:

$$D(t) = \frac{\varepsilon(t)}{\sigma_0} = \frac{2 \cdot bh^2 \cdot \Delta H(t)}{3 \cdot P \cdot l \cdot GL} \quad (1.10)$$

where, $\epsilon(t)$=strain as a function of time, $\sigma_0$=constant stress; $\Delta H(t)$=horizontal deformation with time change; GL=gage length of the extensometer; p=wheel loading; l=length of loading path; b=width of specimen; h=height of specimen.

Experimental Method

Uniaxial Viscoelastic Test

In the uniaxial tests, three types of loading modes, compression, compression-tension, and tension were employed. Three commercially available LVDTs were mounted on each of the three beam specimens under test to measure the axial deformation. A strain gauge, an optical fiber sensor or other known strain measurement device may be used in the alternative. Dynamic modulus tests were conducted at three temperatures, 10, 25, and 40° C. at nine frequencies, 25, 20, 10, 5, 2, 1, 0.5, 0.2 and 0.1 Hz. While creep tests were conducted at 10 and 40° C. with constant loads.

In order to maintain the strain response within the range of linear viscoelasticity, stress amplitude was adjusted based on the material stiffness, temperature, frequency, as well as different loading modes. Typically, a strain level within the range of 50 to 200 microstrains is considered as the range for linear viscoelasticity. The loading was applied at each frequency until steady-state response was achieved, at which point data via data acquisition system 530 were collected for several loading cycles (commonly, the data are collected after 5 pre-loading cycles). After the test in each loading mode, at least 30-minute rest periods were allowed for a specimen to recover before the next test in a different loading mode.

In the uniaxial creep test, the specimen is subjected to a static axial load in both tension and compression modes, and the axial deformation is recorded by the three LVDTs mounted on the same specimen. In order to eliminate the effect of non-uniformity for the axial deformation, an average value was taken on the three LVDTs. Based on static creep test, creep compliance as mentioned earlier can be determined.

LWT Viscoelastic Property Test

Beam samples 300 mm in length, 125 mm in width and 50 mm in height were fabricated by using an Asphalt Vibratory Compactor (AVC) for performing modified LWT viscoelastic property tests according to embodiments and processes described herein. In the test, triplicate beam samples were subjected to the loading wheels in various environmental conditions via an enclosed environmental chamber, and the tensile deformation of each beam specimen was measured by, for example, one or multiple Linear Variable Differential Transformers (LVDTs) mounted at the middle on the bottom surface, as shown in FIG. 14(*a*). Prior to testing, a high range LVDT was mounted on the frame and connected, to the moving arm, for example, by a clustered high strength string for the purpose of recording the location and movement of the wheels over time (FIG. 14(*d*)). Based on the movement of the wheels, the stresses can be calculated (FIG. 14(*b*)). The data of the movement of the wheels and tensile deformations were continuously recorded over time by a data acquisition system 530 during the testing and stored in memory 560 for display. Dynamic modulus and phase angle can be calculated from the stress and measured tensile strain.

For the loaded wheel dynamic modulus test, sinusoidal stress was applied to the samples through moveable loading wheels. A series of loading frequencies ranging from 2, 1, 0.5, 0.2 and 0.1 Hz were employed by specifying the angular frequency of the rotation axis. Moreover, all the asphalt mixtures were tested at three different temperatures, e.g., 10, 25 and 40° C., to construct a master curve representing the values of the dynamic modulus over a range of temperatures and loading frequencies. The stress levels for the loaded wheel dynamic modulus test were 311 kpa (45.4 psi), 170 kpa (24.8 psi) and 74 kpa (10.7 psi) at 10, 25 and 40° C., respectively, regardless of varying the loading frequency. The different magnitude levels of stress were determined in order to limit the recoverable tensile strains within 200 micro-strains. The typical patterns of the sinusoidal stress and measured tensile strain in the loaded wheel dynamic modulus test are shown in FIG. 15.

Figure 16:
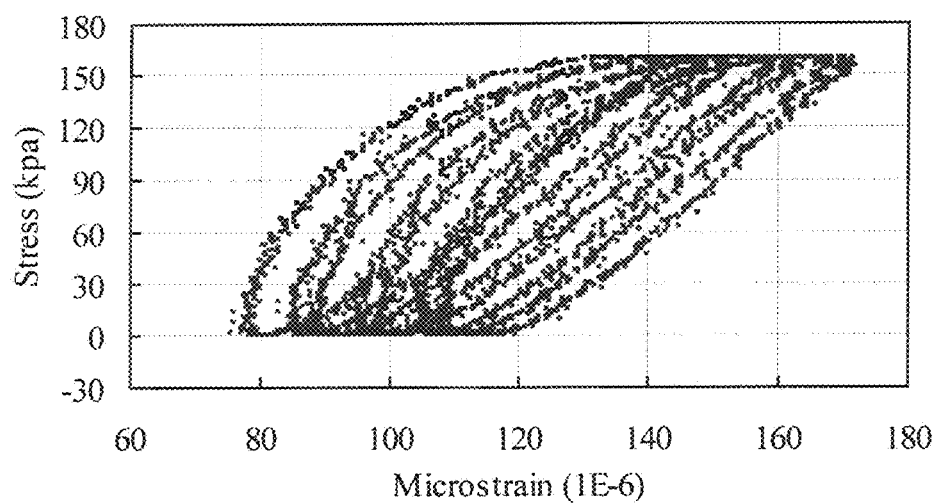
FIG. 16 shows typical hysteresis loops in a loaded wheel dynamic modulus test.

As long as asphalt material behaves linear viscoelastically under loading and unloading, the area of hysteresis loop will not change with the cyclic loadings (Lytton 2000). The typical hysteresis loops in the loaded wheel dynamic modulus test are shown in FIG. 16.

During the loaded wheel creep test, the beam specimen is subjected to a constant load at the middle. Meanwhile, the tensile strain at the middle of the bottom surface of the beam is recorded with a data acquisition system 530. Referring to AASHTO T322 (incorporated by reference herein as to test standards), the loading duration for the creep test has been chosen for 100 seconds. Every specimen was tested three times with 30 minutes' relaxation interval between tests. According to the literature, damage is easily caused to specimens due to dramatically large deformation at high temperatures. Therefore, creep tests were conducted only at 10° C.

and 25° C. Stress levels were chosen to ensure that the final strains would not exceed 500 micro-strains within the 100-second loading time.

Indirect Tension Creep Test

A creep test was also conducted in an indirect tension (IDT) mode to compare the difference of viscous behavior (creep compliance) in different loading modes for asphalt mixtures. During the test, a vertical load was applied on the specimens. The LVDTs when installed in lengthwise and width directions can record the vertical and horizontal deformations during loading and the recovered deformations during unloading (FIG. 5(C)). Cylindrical specimens approximately 150 mm (6 in.) in diameter were first compacted with the Superpave gyratory compactor (SGC) and then cut to 50-mm (2 in.) thickness. The tests were conducted following the procedures specified in AASHTO T322. The details of this test are not provided herein. All dimensions discussed herein should be deemed to be within ranges of plus and minus twenty percent when "approximately" is used in the claims to the invention.

Data Processing

Because of the noise in data acquisition, the measurements obtained from the data acquisition system 530 might not be stable enough, especially for the valleys and peaks. Generally, this problem can be solved using the Savitzky-Golay or the Fast Fourier Transform (FFT) filter smoothing method. The Savitzky-Golay filter method essentially performs a local polynomial regression to determine the smoothed value for each data point. This method is superior to adjacent averaging because it tends to preserve features of the data such as peak height and width, which are usually 'washed out' by adjacent averaging. In comparison, the FFT smoothing allows one to eliminate noise above a specified frequency using a sum of weighted sine and cosine terms of increasing frequency. The data must be equally spaced and discrete smoothed data points will be returned. After comparing those two methods and while Savitsky-Golay or a combination with FFT may be employed to advantage, the FFT filter smoothing method was selected and utilized. The FFT filter smoothing process could be accomplished by removing the Fourier components with frequencies higher than a cut-off frequency expressed below:

$$F_{cutoff} = \frac{1}{n \cdot \Delta t} \quad (1.11)$$

where, n is the number of data points specified by the user, and $\Delta t$ is the time spacing between two adjacent data points. Larger values of n result in lower cut-off frequencies, and thus a greater degree of smoothing. The function used to clip out the high-frequency components is a parabola with a maximum of 1 at zero frequency, which falls off to zero at the cut-off frequency defined above. The example of a stress-strain curve before (FIG. 17(a)) and after (FIG. 17(b)) the FFT smoothing process is shown in FIG. 17, where strain lags stress in both sets of curves.

Materials and Specimen Properties

Four typical asphalt mixtures used in the state of Tennessee were tested. Two types of aggregates (limestone and granite) and three types of asphalt binder grades (PG 64-22, PG 70-22 and PG 76-22) were used. For the mixtures made with granite, only PG 64-22 was used, while all three asphalt binders were used for the mixtures made with limestone. An aggregate structure meeting the Tennessee Department of Transportation (TDOT) specifications for 411-D mixtures was used as a design basis. Both limestone and granite had a nominal maximum aggregate size of 12.5 mm (½ in.). The fine aggregates consisted of No. 10 screenings, natural sand, manufactured sand, agricultural lime and screened recycled asphalt pavement (RAP) material. RAP material used in this, study was obtained from limestone sources and was used as a substitute for the fine aggregate in equal proportions for all the mixtures with limestone, while there was no RAP in the mixtures with granite. Mixtures with limestone aggregates were designed at 5.0 percent of asphalt content, while the mixtures with granite aggregates were designed at 5.8 percent of asphalt content. For simplicity, the term of GN is used to represent granite, LS represents limestone, while the mixture GN-1 stands for the mixture made with granite aggregates and PG64-22 asphalt binder, LS-1 limestone and PG64-22, LS-2 limestone and PG70-22, LS-3 limestone and PG76-22.

The detailed information of the asphalt mixtures is presented in Table 4.

TABLE 4

Asphalt mixtures

| Mixture ID | Aggregate | Asphalt Binder | Asphalt Content |
|---|---|---|---|
| GN-1 | Granite | PG 64-22 | 5.8% |
| LS-1 | Limestone | PG 64-22 | 5.0% |
| LS-2 | Limestone | PG 70-22 | 5.0% |
| LS-3 | Limestone | PG 76-22 | 5.0% |

The detailed information of the specimens for the tests are provided in Table 5.

TABLE 5

Specimens for the tests

| Test | Specimen Type | Compaction Method | Air Voids (%) |
|---|---|---|---|
| IDT | 150 * 50 mm cylindrical pill | Superpave Gyratory Compactor (SGC) | 4 ± 1 |
| Uniaxial | 100 * 150 mm cylinder | Superpave Gyratory Compactor (SGC) | 4 ± 1 |
| LWT | 300 * 125 * 50 mm beam | Asphalt Vibratory Compactor (AVC) | 5 ± 1 |

Viscoelastic Property Results and Discussion

Creep Test

Figure 18:
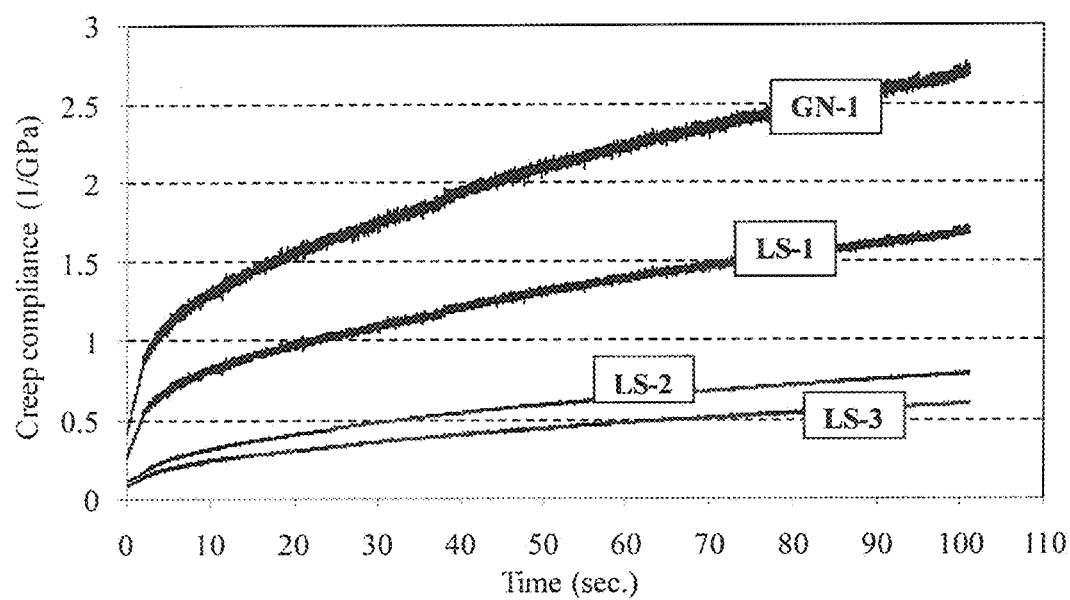
FIG. 18 shows creep compliance curves from a loaded wheel creep test (10° C.).

As an example, the typical creep compliances of the different asphalt mixtures obtained from the loaded wheel creep test at 10° C. (best temperature) are shown in FIG. 18. From the creep compliance results, the increase of deformation for the mixtures under a constant load (stress) can be reflected. The deformation increased rapidly in the beginning of the test. The increase in deformation tended to slow down with the increase in time. From those curves, the creep behavior of the mixtures could be differentiated and identified.

FIG. 19 shows the results of the creep test with different testing methods at 10° C. and 25° C. The creep compliances were calculated using the creep deformation at the 100th second. The creep compliance values obtained with different creep tests were different due to the differences in loading geometry, loading condition, and air voids content of the specimen under test. However, the ranking of the creep compliance for the four mixtures was consistent among the different creep tests. The results from the LWT creep test were generally in agreement with those from other tests, indicating that the LWT creep test was able to identify the mixtures with different viscoelastic properties. The mixture LS-3 with the highest performance grade (PG) of asphalt binder (PG 76-22)

had the lowest creep compliance, which represents a highest ability to resist creep deformation. The mixture GN-1 with a higher asphalt content showed higher creep compliances, which indicates that higher asphalt content would lead to a reduction in the creep resistance of asphalt mixtures. From FIG. 19, all the asphalt mixtures exhibited higher creep deformation resistances (lower creep compliances) in the uniaxial compression mode than in the uniaxial tension mode, at both 10° C. and 25° C.

Dynamic Modulus Test

Figure 26:
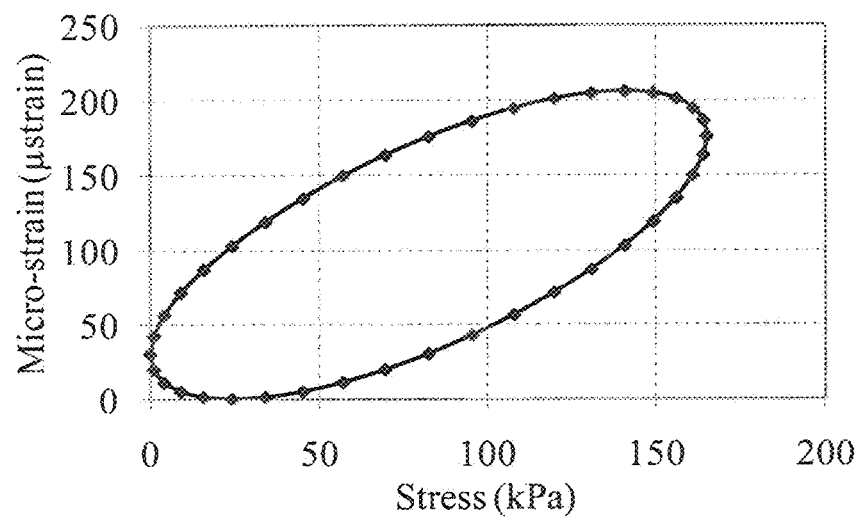
FIG. 26 shows a typical stress-strain hysteresis loop.

From the dynamic modulus results shown in FIG. 26, the same ranking of the mixtures in terms of dynamic modulus results was shown in the different dynamic modulus tests. This ranking is also consistent with the ranking in terms of creep compliance.

Figure 21:
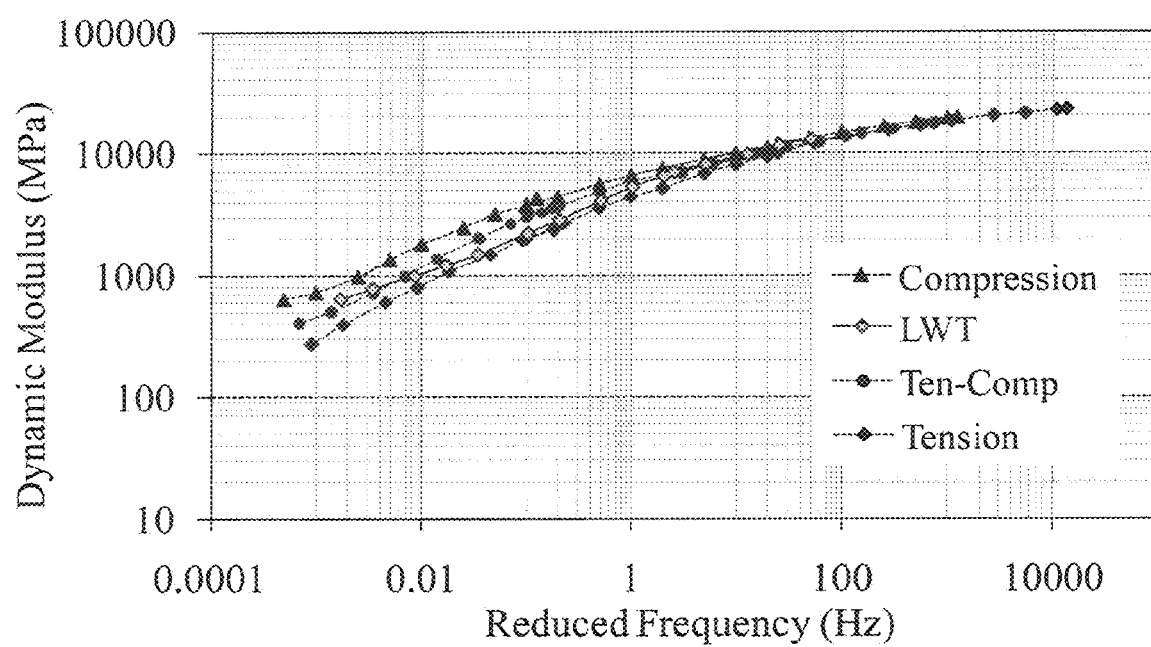
FIG. 21 shows dynamic modulus master curves in different loading modes for asphalt mixture LS-3.

Comparing the results for various mixtures shown in FIG. 20, the higher the high temperature grade of asphalt binder, the greater the dynamic modulus was. Due to the highest stiffness, the mixture LS-3 with polymer modified asphalt binder, PG 76-22, obtained the highest dynamic modulus among all the mixtures tested. On the other hand, the mixture GN-1 had the smallest dynamic modulus because of its lowest stiffness. Considering the difference between the mixtures with different aggregate types, all the mixtures with limestone aggregate base exhibited higher dynamic moduli than the mixture made with granite. In the different loading modes of the uniaxial test, dynamic moduli of the four mixtures followed similar trends under tension, tension-compression, and compression testing conditions. The dynamic modulus decreased more rapidly at high temperatures in tension mode than that in tension-compression and compression modes, which can be observed from the tails of the master curves at low frequencies. As an example, the dynamic modulus master curves for LS-3 in different testing modes are shown in FIG. 21.

FIG. 22 presents the dynamic modulus discrepancy at 40° C., 0.1 Hz and 10° C., 2 Hz among different mixtures and the different loading modes of uniaxial testing.

The dynamic moduli from 0.01 Hz to 2 Hz at high temperature (40° C.) in tension were only 40-60% of those obtained in compression and 65%-85% of those in tension-compression. However, the dynamic moduli obtained in tension at low temperature (10° C.) were 7%-10% higher than those obtained in tension-compression and 15%-30% higher than those in, compression. The reasons for this phenomenon are that the tensile stress was primarily resisted by asphalt bonding, while the compressive stress was more supported by aggregate structure than by asphalt. This indicates that aggregate, which is much stiffer than asphalt, contributes more than asphalt to the dynamic modulus of asphalt mixtures in compression, while asphalt contributes more to the dynamic modulus of asphalt mixtures in tension than aggregate. In addition, as a viscoelastic material, asphalt binder becomes soft at higher temperatures and stiff at low temperatures. All temperatures suggested herein and the like should be considered to be exemplary of a reasonable test temperature and temperature range and may have been used for compliance with known test standards. Temperatures in a particular region of the world may be much higher at the equator and much colder in colder climates and so appropriate temperatures for testing may be selected accordingly.

Phase Angle

The phase angle results for the uniaxial tests and LWT tests are shown in FIG. 23. From FIG. 23, the asphalt mixtures made with higher asphalt grade exhibited smaller phase angles.

In FIG. 24, the mixtures LS-2 and LS-3 were chosen to show the effect of loading mode on phase angle. The phase angles in tension were considerably greater than those in tension-compression and compression at high temperatures, but the differences reduced gradually with the decrease of temperature. The phase angle results indicate that asphalt binder made a greater contribution to the viscous properties of asphalt mixtures in tension than in tension-compression and compression, especially at high temperatures.

The phase angle results from the loaded wheel test at high temperatures, which correspond to low frequencies, generally fell between the results from uniaxial tension and tension-compression tests. However, there was no consistent relationship of phase angles between loaded wheel tests and uniaxial tests at low temperature (high frequencies), in which the phase angles obtained in loaded wheel tests were greater than those from uniaxial tests.

Summary for Viscoelastic Property Testing

An innovative flexural testing method characterizes the viscoelastic behaviour of asphalt mixtures by using a modified loaded wheel tester (LWT). The detailed analysis for the mechanical system and the procedures to perform the test are discussed above. In order to verify the applicability of a loaded wheel test for testing viscoelastice property of asphalt mixtures, a uniaxial test in tension, tension-compression and compression modes, and an indirect tension test were also conducted for comparison with the results from a modified LWT.

As two major approaches to investigate the viscoelastic properties of asphalt mixture, dynamic modulus and creep tests have been carried out. Unlike the conventional testing methods for those two tests, a loaded wheel test provides more realistic loading conditions than other test methods. Based on the results from this study, the following conclusions and summary can be obtained:

1. The results showed that loaded wheel tests were able to characterize the viscoelastic properties of asphalt mixtures, which may be affected such factors as asphalt content, types of aggregate and asphalt binder. The modified LWT could provide viscoelastic property results consistent with those from known tests.
2. As discussed above, some differences existed between the uniaxial tests in tension and compression, especially when the test was conducted at high temperatures. In tension mode, asphalt binder plays a main role in resisting the deformation induced by external load, while in compression, the load is mainly carried by aggregate skeleton structure through the interlocking action among aggregate particles.
3. The modified LWT viscoelastic property test had a high efficiency because three samples could be tested simultaneously. Moreover, phase angle was calculated over time. The fabrication process of test specimens for LWT testing is relatively simple and convenient.

Fatigue Testing

Fatigue testing will now be discussed with reference to FIGS. 25-34. A number of test methods have been developed for characterizing the fatigue behavior of asphalt mixtures, which include diametric fatigue, beam flexural fatigue test, and tests employing the fracture mechanics principle. The primary factor affecting fatigue response is whether the fatigue test is conducted in a stress-controlled or strain-controlled mode (Tangella et al. 1990). Among different tests, axial compression or tension fatigue test, an indirect tension test and a beam flexural fatigue test are the most widely used tests in recent years.

Figure 25:
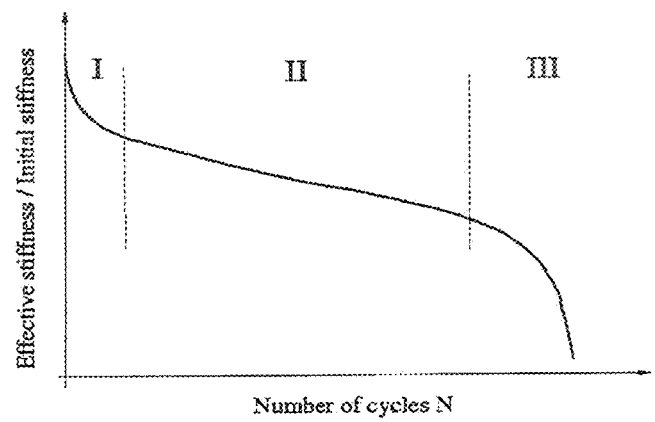
FIG. 25 shows typical developing phases in a fatigue test.

During fatigue tests, the stiffness, calculated as the ratio of the stress to the strain amplitude, decreases, following three regimes of evolution, as shown as FIG. 25. Rapid decrease in stiffness can be observed in Phase I, followed by a nearly linear stiffness decrease in Phase II. While in phase III, fracture cracking will occur due to the damage acceleration of micro-cracks and ultimately turn to observable macro-cracks, which will cause the failure of the materials.

Most of the known fatigue models are related to the horizontal tensile strain and stiffness of the asphalt mixture. Considerable research has been focused on the fatigue characteristics of asphalt concrete mixtures through fatigue testing. Some researchers report that the stress-controlled testing is generally related to relatively thick pavement construction where high stiffness is the fundamental parameter that underpins fatigue life. Strain controlled testing is thought to be associated with thin asphalt pavements where the elastic recovery properties of the material have the fundamental effect on its fatigue life. Recent studies generally recommend the strain-controlled test to evaluate the fatigue resistance of asphalt mixes. In a strain-controlled test, the failure of the specimen can be defined as a 50 percent reduction in initial stiffness. In addition, there are several criteria for modeling asphalt concrete fracture using the concept of dissipated energy ratio or damage accumulation ratio. The change of phase angle during the fatigue process has also been used to reflect the failure point.

Conventional Fatigue Tests for Asphalt Mixtures
Flexural Beam Fatigue Test

The flexural beam fatigue test, also called a four-point repeated bending beam test, is standard test method for determining the fatigue life of compacted asphalt mixtures subjected to repeated flexural bending (AASHTO T321; ASTM D 7460), incorporated by reference herein. The Strategic Highway Research Program (SHRP) Project A-003A made significant advancements in testing and evaluating the fatigue resistance of asphalt mixtures by using this test method. This test uses digitally controlled pneumatic beam fatigue equipment, which subjects a beam specimen to a repeated stress-controlled or strain-controlled load applied at the center of the beam until failure occurs.

In the flexural beam fatigue test, one of the failure criteria is that the stiffness of the specimen reaches half (50%) of its initial value. The test is terminated automatically when the reduction of stiffness reaches 50%. The magnitudes of stress, strain, stiffness and phase angle can be determined by the formulas shown as follows:

$$\sigma_t = \frac{3aP}{wh^2} \quad (1.12)$$

$$\varepsilon_t = \frac{12h\delta}{3L^2 - 4a^2} \quad (1.13)$$

$$S = \frac{\sigma_t}{\varepsilon_t} \quad (1.14)$$

$$\phi = 360 \cdot f \cdot s \quad (1.15)$$

where, $\sigma_t$=peak-to-peak stress; $\varepsilon_t$=peak-to-peak tensile strain; P applied peak-to-peak load; S=stiffness; L=beam span; w=beam width; h=beam height; $\delta$=beam deflection at neutral axis, and a=L/3.

Direct Tension Fatigue Test

The direct tension test provides a direct measurement of the fatigue behavior of asphalt concrete under cyclic tensile loading. The testing set up is the same as that in the direct tension dynamic test previously discussed. Generally, the cylindrical specimens 100 mm (4 in.) in diameter and 100 mm (4 in.) high are prepared with the gyratory compaction method. Three LVDTs are glued at 120° on the specimens to measure the vertical deformation. During the test, specimen is subjected to uniaxial tensile repeated loading which give the specimens a relatively uniform tension strain in the central section. The pattern of the repeated loading can be controlled by known MTS Systems processes (Eden Prairie, Minn.) though either strain or stress control.

Interpreting Fatigue Behavior of Asphalt Mixtures

Many researchers studied the fatigue properties of asphalt materials in the second half of the last century. One of the most important ways to describe the material's behavior during cyclic loading is based on the analysis of stress and strain. With stress and strain, the hysteresis loop can be constructed, which is one of the most important analytical tools in the study of fatigue. For a viscoelastic material like asphalt mixture, the most important property of its hysteresis loops is not their ability to show cyclically varying stress and strain but their ability to reflect the plastic strain caused during the loading-unloading cycles. A typical stress-strain hysteresis loop is shown in FIG. 26.

Dissipated Energy Method

When asphalt mixture is subjected to an external load, the area of the hysteresis loop represents the energy dissipated during fatigue testing. The dissipated energy causes damage to the specimens through one or more damage mechanisms, such as the initiation and propagation of micro cracks which eventually turn into macro cracks, permanent deformation as well as heat transmission. As such, dissipated energy becomes an effective way to determine whether a system is non-damaged or damaged (suggesting use of a test specimen temperature sensor). For a system subjected to fatigue cracking, or deteriorating, the energy dissipation cannot be maintained to be constant under cyclic loading because, as the loading cycle increases and the cracks propagate, the dissipated energy changes continuously. Therefore, the concept of dissipated energy (DE) can be used as a direct way to describe the fatigue behavior of asphalt mixtures during cyclic loading. Dissipated Energy per cycle can be calculated as $$DE = \pi \sigma_n \varepsilon_n \sin \phi_n \quad (1.16)$$

where, $\sigma_n$=stress at loading cycle n; $\varepsilon_n$=strain at loading cycle n; and $\phi_n$=phase angle between stress and strain at loading cycle n.

Figure 27:
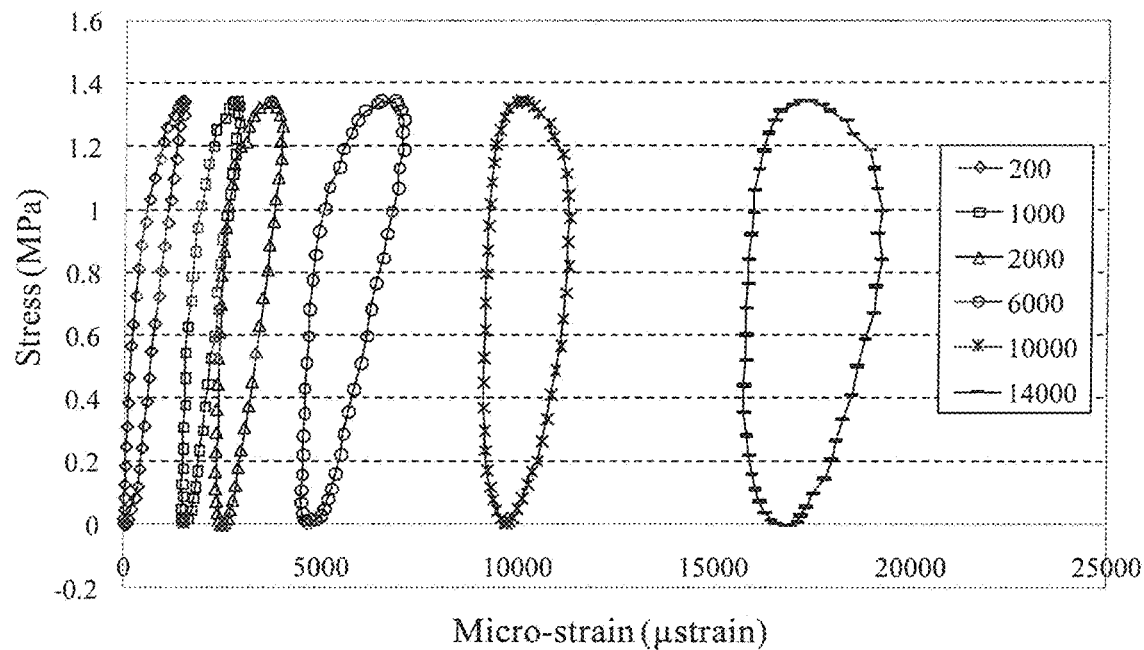
FIG. 27 shows hysteresis loops at various cycles (from a modified loaded wheel test).

Dissipated energy can also be calculated in the numerical way by determining the area of the hysteresis loops (FIG. 27).

Many researchers have employed the dissipated energy approach to study the fatigue characteristics of asphalt mixtures. Baburamani and Porter (1996) correlated the fatigue life with the initial dissipated energy. Van Dijk and Vesser (1977) found that there exists a strong relationship between the total amount of energy dissipation and the number of loading cycles to failure. This relationship is not significantly affected by the loading modes, frequency, temperature, and occurrence of rest periods, but is highly dependent on material type. Tayebali et al. (1992) introduced two terms, stiffness ratio and dissipated energy ratio. The stiffness ratio is defined as the ratio of the stiffness at load cycle to the initial stiffness, and the dissipated energy ratio is defined as the ratio of cumulative dissipated energy up to load cycle to the cumulative dissipated energy up to fatigue life. Their work suggests that there is a unique relationship between the stiffness ratio and the dissipated energy ratio, but not necessarily between cumulative dissipated energy and fatigue life. The relationship has been verified by the Strategic Highway Research Program (SHRP) A-404 (1994) and Fakhri (1997). This relationship was found to be mixture and temperature dependent.

Ratio of Dissipated Energy Change Approach

More recent studies suggest that more consistent results can be achieved through the concept of the Ratio of Dissipated Energy Change (RDEC) (Carpenter et al., 2003; Ghuzlan and Carpenter, 2000; Shen and Carpenter, 2005). This concept was first initiated by Carpenter and Jansen (1997), who suggested using the change in dissipated energy to relate damage accumulation and fatigue life. The change in dissipated energy represents the total effect of fatigue damage without the necessity of considering material type, loading modes and severity separately. The concept was later modified and expanded by Ghuzlan and Carpenter (2000) and Carpenter et al. (2003). RDEC is expressed as the following formula:

$$RDEC = \frac{DE_{n+1} - DE_n}{DE_n} \quad (1.17)$$

where, RDEC=ratio of dissipated energy change; $DE_n$=dissipated energy in load cycle n; and $DE_{n+1}$=dissipated energy in load cycle n+1.

Figure 28:
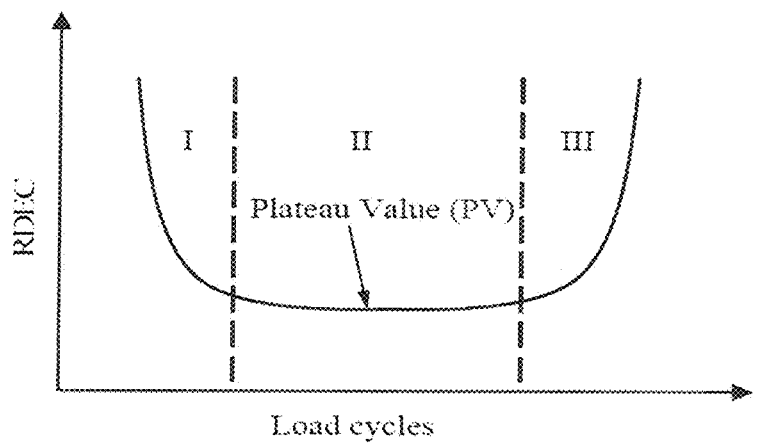
FIG. 28 shows a typical ratio of dissipated energy change (RDEC) vs. load cycle curve.

FIG. 28 shows the typical pattern of an RDEC plot with increasing load cycles. From the RDEC plot, a Plateau Value (PV) can be determined. This PV value represents a period where there is a constant percent of input energy being turned into deformation damage. The smaller the PV value, the longer the fatigue life for a mixture. The PV value is a function of the load inputs for any mixture and it varies with mixture type for similar load inputs. The PV value provides a unique relationship with fatigue life for different mixtures, loading modes and loading levels (Shen et al. 2006).

The fatigue life can be characterized by a plateau value (PV) and a number of loading cycles at 50% of initial stiffness failure. It was found that 500,000 cycle load repetitions were sufficient to ensure that a stable plateau stage is reached. A lower PV value usually represents longer fatigue life of the mixture.

The RDEC approach was employed to analyze the fatigue behaviour of asphalt mixtures. Shen (2006) reported that a unique relationship can be established between PV and $N_f$ regardless of the asphalt mixture type, the loading mode and testing condition.

Laboratory Testing

A loaded wheel fatigue test for asphalt mixtures utilizing a modified loaded wheel tester (LWT) will now be discussed. The LWT fatigue test was conducted using a modified LWT on an APA platform of Pavement Technology, for example, including a means for determining loaded wheel location over time. In the LWT fatigue test, beam specimens are subjected to cyclic loads applied by the moving wheels of APA, while LVDTs are installed at the middle of the bottom surface of the specimens to measure the tensile strains induced by the cyclic loads. Other strain measuring devices may be used to advantage such as an optical fiber sensor which may be used when a specimen is submerged in water to simulate a heavy rain storm. Compared to the conventional APA fatigue test, the present method embodiment can determine the fatigue life of specimens through theoretical analyses of dissipated energy or stiffness.

Figure 29:
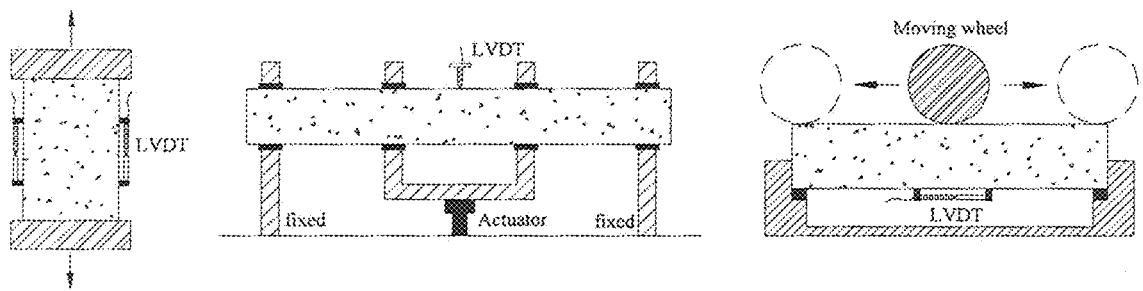
FIG. 29 shows a sketch of the setups for three different fatigue tests.

In order to verify the rationality of loaded wheel fatigue test, two conventional fatigue tests, direct tension fatigue test and flexural beam fatigue test, were conducted. The sketches of the testing setup for the three types of fatigue tests are shown in FIG. 29 where the LWT fatigue test is shown as FIG. 29(c).

Compared to other fatigue tests, the LWT fatigue test has the following benefits: (1) the loading condition of specimen is consistent with actual situations on real pavements; (2) the process of specimen fabrication and testing preparation are relatively simple and convenient; (3) three specimens can be tested simultaneously in both dry and water submerged conditions at different temperatures, for example, via use of an environmental chamber surrounding the LWT.

The information for these three fatigue tests is presented in Table 6.

TABLE 6

Fatigue tests in this study

| Type | Test name | Testing temperature | Frequency | Testing Equipment |
|---|---|---|---|---|
| Conventional | Direct tension | 10° C. | 2 Hz | Material Testing System (MTS) |
| | Flexural beam (AASHTO T321) | 10° C. | 10 Hz | Beam Fatigue Apparatus (BFA) |
| Modified | Loaded wheel | 10° C. | 2 Hz | Asphalt Pavement Analyzer (APA) |

Specimen Preparation

The detailed information of the specimens prepared for the fatigue tests is provided in Table 7. Two different methods of compaction were used. The beam specimens for flexural beam fatigue test need to be cut from the original specimens compacted with the asphalt vibratory compactor (AVC). The cylindrical specimens for direct tension test need to be cored and trimmed from the original cylindrical specimens compacted with SGC.

TABLE 5.1

Specimen for fatigue tests

| Test | Specimen Type | Compaction Method | Air Voids (%) |
|---|---|---|---|
| Flexural beam | 380 * 50 * 63 mm beam | Asphalt Vibratory Compactor (AVC) | 4 ± 1 |
| Direct tension | 100 * 150 mm cylinder | Superpave Gyratory Compactor (SGC) | 4 ± 1 |
| Loaded wheel | 300 * 125 * 50 mm beam | Asphalt Vibratory Compactor (AVC) | 5 ± 1 |

Uniaxial Direct Tension Fatigue Test

The test setup for the uniaxial direct tension fatigue test is the same as that previously described in the section "Direct tension test for viscoelastic properties". Before testing, specimens were placed in the environmental chamber specified at 10° C. for at least two hours so that the specimens reached the test temperature. During the testing, the specimen is subjected to a cyclic tension load at the frequency of e.g. 2 Hz. The axial tension deformation is measured with the LVDTs mounted on the surface of the specimen.

Flexural Beam Fatigue Test

In the flexural beam fatigue test, a constant strain level was applied to the beam specimen at a loading frequency of 10 Hz such that the specimen will undergo a minimum of 10,000 load cycles. Each specimen was tested in strain-controlled mode at 600 micro-strains at the center of the beam until a stable Plateau Value (PV) region was reached. Also, the 50% reduction in initial stiffness method specified in the AASHTO T 321-03 test method was used to evaluate the fatigue life of the asphalt mixtures.

Loaded Wheel Fatigue Test

The loaded wheel fatigue test was conducted by subjecting the specimens to the cyclic loads applied by moving wheels. The LWT fatigue test was performed at 10° C. and at the loading frequency of 2 Hz. The tensile strain induced by the moving wheels could be measured through the LVDTs mounted on the bottom surfaces of the beam specimens.

Results and Discussion

Reduction of Stiffness

Figure 30:
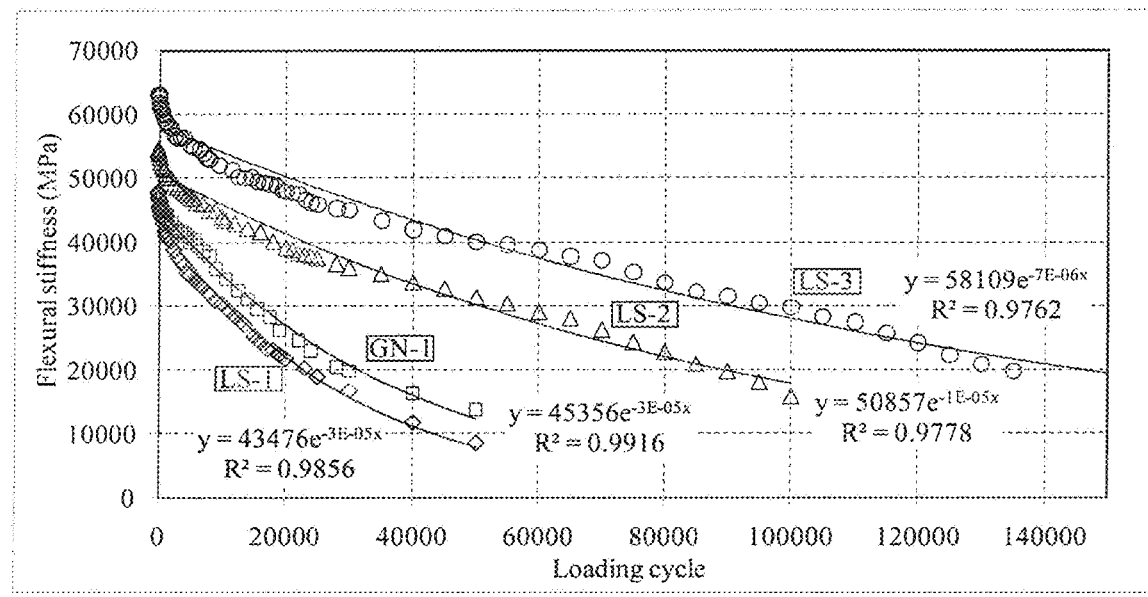
FIG. 30 shows change of stiffness with increasing loading cycle in various fatigue tests.

FIG. 30 shows the change in the stiffness with the increase in loading cycle for the different fatigue tests.

The trends of the stiffness vs. loading cycles curve plots were similar for all three fatigue tests. The curves could be generally divided into three regions: an initial rapid reduction in stiffness followed by a much slower reduction and a final more rapid reduction prior to failure. The mixtures made with higher asphalt binder grades showed higher stiffness and their fatigue lives (number of loading cycle to failure) were also longer.

Figure 31:
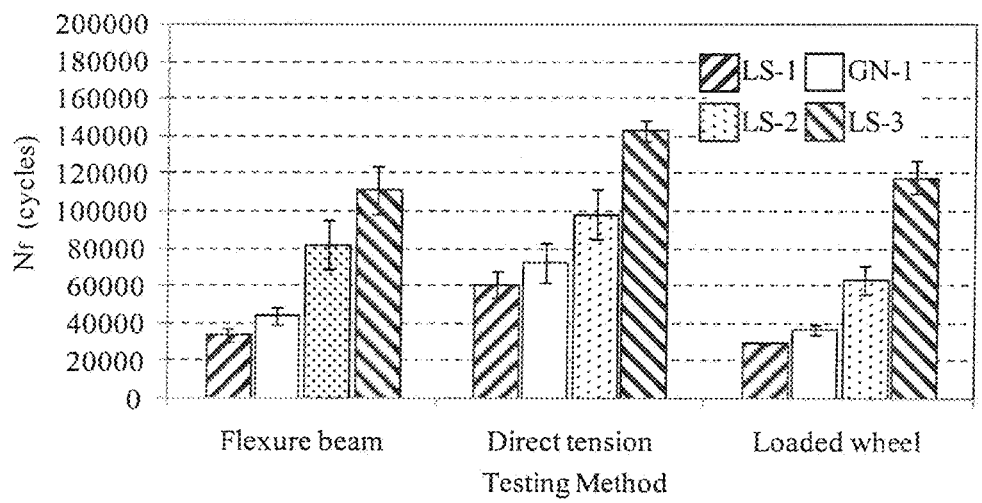
FIG. 31 shows $N_f$ results from different fatigue tests for various mixtures.

FIG. 31 shows the $N_f$ (number of loading cycles to failure) results of the asphalt mixtures determined with the 50% initial stiffness reduction method. This method determines that failure occurs once the stiffness of a specimen has reached 50% of its initial value. The fatigue life is defined as the number of loading cycles ($N_f$) the specimen has undergone before failure occurs.

FIG. 31 shows that the three fatigue tests gave the same ranking in the fatigue life of asphalt mixtures; i.e., mixture LS-3 had the longest fatigue life among all the mixtures followed by mixtures LS-2, GN-1, and LS-1. The ranking of the asphalt binder PG grade in the limestone mixtures was consistent with the fatigue life ranking of their fatigue life, indicating that higher asphalt binder PG grade led to higher initial stiffness and longer fatigue life. The initial stiffness of Mixture GN-1 was smallest among all the mixtures. However, with a higher asphalt content of 5.8%, GN-1 had a longer fatigue life than mixture LS-1 with a asphalt content of 5%, indicating that a higher asphalt binder content had a positive influence on the fatigue life of asphalt mixtures.

Ratio of Dissipated Energy Change (RDEC)

Figure 32:
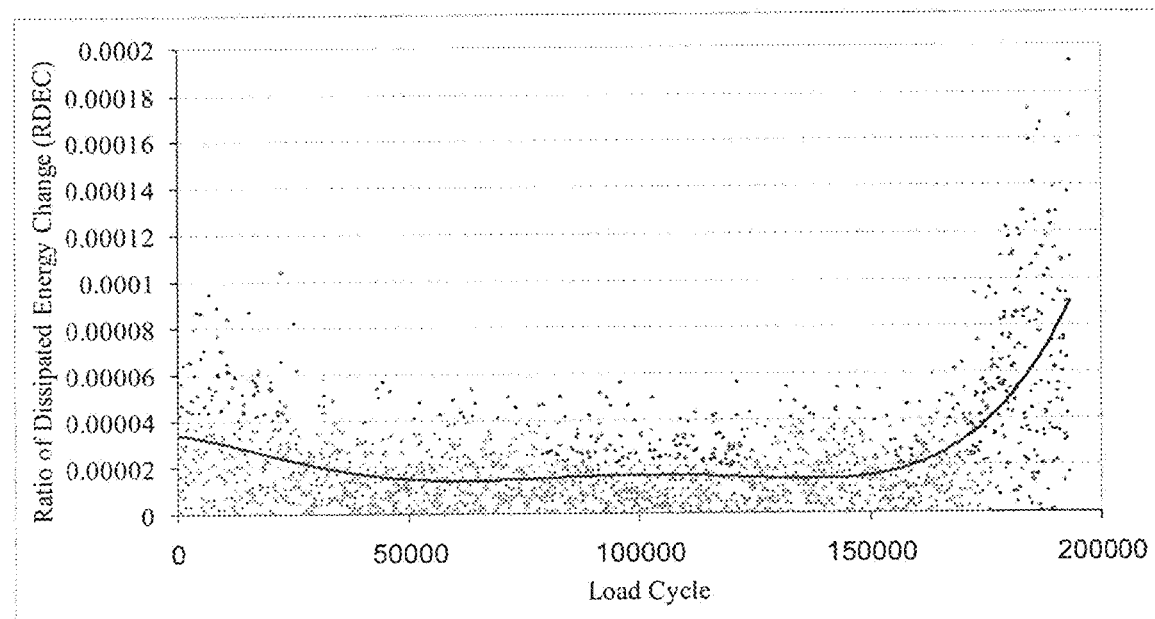
FIG. 32 shows change of RDEC with increasing load cycle.
Figure 33:
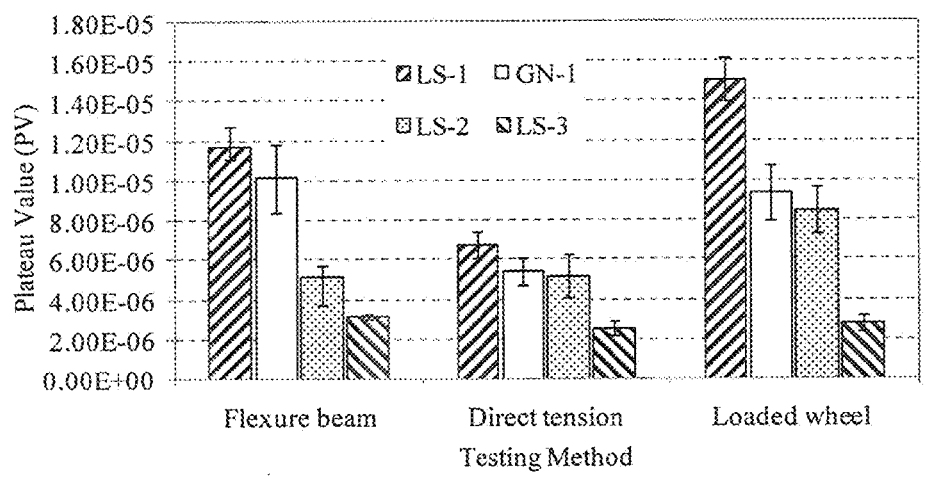
FIG. 33 shows plateau value results from different fatigue tests for various mixtures.

The procedures proposed by Shen (2006) were used to calculate RDEC and PV for the different fatigue tests. FIG. 32 shows a typical RDEC vs. load cycle plot. FIG. 33 shows the PV results of asphalt mixtures from different fatigue tests.

FIG. 33 shows that the PV results of from the modified LWT fatigue test were in good agreement with those from the known flexural beam and direct tension fatigue tests. The fatigue lives of mixtures in terms of PV were generally in consistent with those represented by $N_f$. The mixtures made with higher grade asphalt binders (such as LS-3 and LS-2) exhibited lower PVs, which implied that they could have longer fatigue lives than other mixtures. Mixture GN-1 had a higher asphalt content and showed a lower PV than mixture LS-1, indicating that GN-1 could have a longer fatigue life than LS-1.

Figure 34:
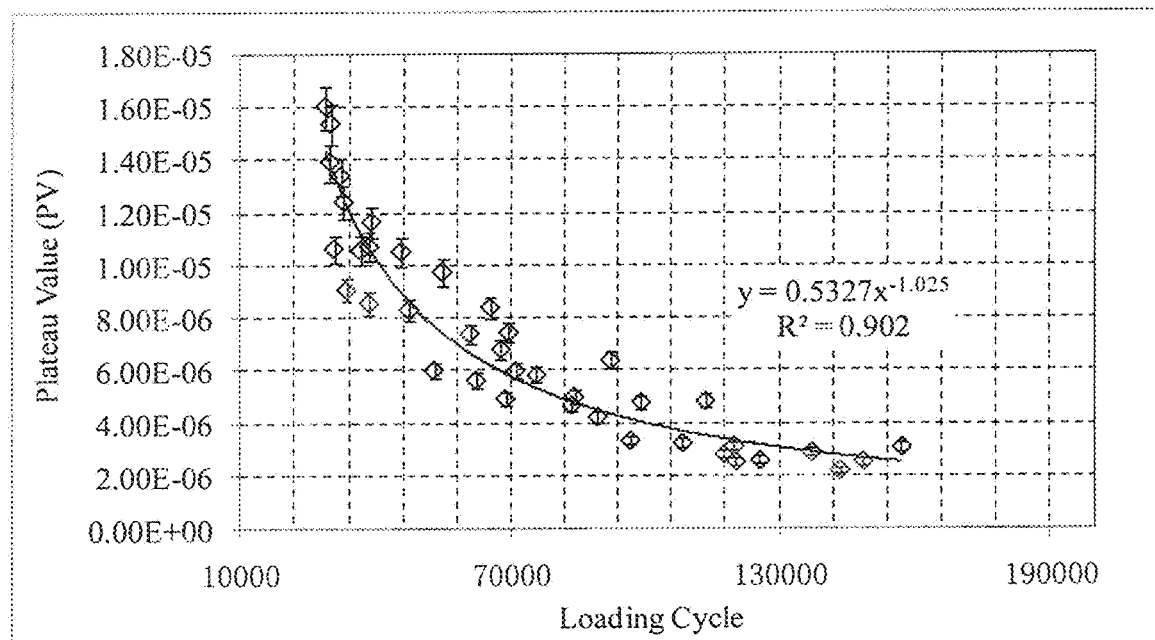
FIG. 34 shows the relationship between PV and $N_f$.

FIG. 34 shows the relationship between PV and $N_f$. An exponential function was found to fit the relationship between PV and $N_f$ very well. Shen (2006) also reported similar relationships. This relationship was found to be independent of mixture type, loading mode (stress or strain-controlled), and testing method.

Summary for LWT Fatigue Testing

A LWT fatigue testing method is proposed to utilize a modified LWT to evaluate the fatigue properties of asphalt mixtures. The modified LWT has unique advantages for simulating the field condition that asphalt materials are subjected to in the actual pavement. Therefore, the test results from LWT fatigue tests are more reasonable to reflect the actual fatigue behavior of asphalt mixtures than other fatigue tests.

The LWT fatigue test was able to differentiate between different asphalt mixtures in terms of fatigue resistance. The results from the LWT fatigue test were consistent with those from flexural beam and direct tension fatigue tests. The results, clearly indicated that the mixtures made with a higher grade of asphalt binder showed higher initial stiffness and a longer fatigue life. The mixtures made with higher asphalt content exhibited a low PV value and a longer fatigue life.

Compared to the old version of APA fatigue test, the proposed LWT fatigue test was more reasonable to characterize the fatigue behavior of asphalt mixtures. In this modified test, theoretical approaches for modeling the fatigue behavior of asphalt mixtures are able to be adopted once the stress and strain are known.

In the direct tension fatigue test, the tensile load is applied to the specimen in the same direction as that the specimen is compacted. However, in the LWT fatigue and flexural beam fatigue tests, the direction of the tensile stress is perpendicular to the direction of the specimen compaction, which is closer to the actual situation in the field. The difference in the internal stress may result in the difference in fatigue behavior of asphalt mixtures.

Thus there has been discussed above apparatus and method embodiments for fatigue and viscoelastic property testing of asphalt mixtures using a modified loaded wheel tester. Other embodiments not specifically described herein may come to mind of one of ordinary skill in the art. While various aspects of the present invention have been described above, it should be understood that they have been presented by way of example and not limitation. It will be apparent to persons skilled in the relevant art(s) that various changes in form and detail can be made therein without departing from the spirit and scope of the present invention. Thus, the present invention should not be limited by any of the above described exemplary aspects, but should be defined only in accordance with the following claims and their equivalents.

In addition, it should be understood that the figures in the attachments, which highlight the structure, methodology, functionality and advantages of the present invention, are presented for example purposes only. The present invention is sufficiently flexible and configurable, such that it may be implemented in ways other than that shown in the accompanying figures. Technical articles and standards referenced above should be deemed incorporated by reference herein as to any material believed necessary to one of ordinary skill to understand the invention.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present; invention in any way. Embodiments should only be deemed limited by the scope of the claims which follow.

BIBLIOGRAPHY

AASHTO, (2003) "T 321-03: Determining the Fatigue Life of Compacted Hot-Mix Asphalt (HMA) Subject to Repeated Flexural Bending." Standard Specifications for Transportation Materials and Methods of Sampling and Testing, Part II, American Association of State Highway and Transportation Officials, Washington D.C.

AASHTO, (2007), "T 322: Standard Method of Test for Determining the Creep Compliance and Strength of Hot-Mix Asphalt (HMA) Using the Indirect Tensile Test Device." American Association of State Highway and Transportation Officials, Washington D.C.

ASTM D 7460, "Standard Test Method for Determining Fatigue Failure of Compacted Asphalt Concrete Subjected to Repeated Flexural Bending, 2010, 14 pages Baburamani, P. S., and Porter, D. W. (1996). "Dissipated Energy Approach to Fatigue Characterisation of Asphalt Mixes." Proceeding of Combined 18th ARRB TR Conference Transit New Zealand Symposium, Part 2, pp. 327-347.

Carpenter, S. H., and Jansen, M. (1997). "Fatigue Behavior Under New Aircraft Loading Conditions." Proceedings of Aircraft Pavement Technology in the Midst of Change, pp. 259-271.

Carpenter, S. H., Ghuzlan, K., and Shen, S. (2003) "Fatigue Endurance Limit for Highway and Airport Pavements." Transportation Research Record 1832, Transportation Research Board, Washington D.C., pp. 131-138.

Fakhri, M. (1997). "Characterisation of Asphalt Pavement Materials," Ph.D. Thesis, The University of New South Wales, Sydney, Australia.

Ghuzlan, K, and Carpenter, S. H. (2000). "An Energy-Derived/Damage-Based Failure Criteria for Fatigue Testing." *Transportation Research Record* 1723, Transportation Research Board, Washington D.C., pp. 141-149.

Lytton, "Characterizing Asphalt Pavements for Performance," *Transportation Research Record: Journal of the Transportation Research Board*, (2000), vol. 1723, pp. 5-16.

Shen, S., and Carpenter, S. H. (2005). "Application of Dissipated Energy Concept in Fatigue Endurance Limit Testing." Transportation Research Record, Issue 1929: 165-173:

Shen, S., (2006). "Dissipated energy concepts for HMA performance: Fatigue and healing". Ph.D. Thesis, University of Illinois at Urbana-Champaign, Urbana, Ill.

Strategic Highway Research Project (SHRP) A-003A, "Summary Report of Fatigue Response of Asphalt Mixtures," 1990, 158 pages Strategic Highway Research Program (SHRP) A-404 (1994), "Fatigue Response of Asphalt-Aggregate Mixes, 310 pages Tangella, R., Crauss, J., Deacon, J. A., and Monismith, C. L. (1990). "Summary report of fatigue response of asphalt mixtures." Institute of Transportation Studies.

Tayebali, A. A., Rowe, G. M., and Sousa, J. B. (1992). "Fatigue Response of Asphalt Aggregate Mixtures." Proceedings of Asphalt Paving Technologists, Vol. 62, pp. 385-421.

Van Dijk, W., and Visser, W. (1977). "The Energy Approach to Fatigue for Pavement Design." Proceedings of Annual meeting of the Association of Asphalt Paving Technologists (AAPT), Vol. 46, pp. 1-40.

What we claim is:

1. A loaded wheel tester comprising;
a moveable loaded wheel adapted for cyclically moving on a test sample of a pavement mixture, a data acquisition system adapted to be coupled to the loaded wheel and to the test sample, a data processor connected to the data acquisition system and an output device for providing test results, the loaded wheel having a central axis receiving a load comprising a vertical nodal force which in turn is adapted to be applied to the pavement mixture test sample,
the loaded wheel tester being characterized by:
the data acquisition system comprising a first transducer for measuring a horizontal deformation via strain directed orthogonal to the vertical nodal force applied to the pavement mixture test sample under the cyclical loaded wheel movement load, the pavement mixture test sample being in the shape of a block adapted to be supported at each end, the block having a length in the direction of loaded wheel movement adapted to receive a cyclically moving load of the loaded wheel, the block length being greater than its width, the first transducer adapted to be mounted at approximately the center of the bottom surface of the block, the supporting of the block at each end creating a space under the test sample block, the first transducer converting the cyclically moving load to electrical signals proportional to strain, the cyclically moving load permitting vertical sample deformation and the data acquisition system further comprising a second transducer connected to the loaded wheel tester for converting a location of the loaded wheel over time to an electrical signal, the stress at the approximate bottom center of the specimen being obtained from the location of the loaded wheel utilizing linear elastic calculation;
the data processor being a special purpose computer processor, responsive to the electrical signals proportional to strain of the first transducer and the electrical signal of the second transducer for obtaining stress, outputting the strain electrical signals to the output device, the output device comprising a display for displaying a hysteresis loop of stress versus strain over time.

2. The loaded wheel tester as recited in claim 1 comprising loaded wheel test stations adapted to receive a test sample block of a pavement mixture having its width dimension being approximately three times a width dimension of the loaded wheel of the loaded wheel test station.

3. The loaded wheel tester as recited in claim 1 further comprising an environmental chamber whereby environmental temperature of the test sample block of the pavement mixture may be selectively controlled to a predetermined temperature within a range of temperatures between 10° C. and 40° C.

4. The loaded wheel tester as recited in claim 3 wherein the environmental chamber permits submersion of the block test sample in water and the first transducer is replaced with an optical fiber sensor adapted to measure strain orthogonal to the vertical nodal force under water.

5. The loaded wheel tester as recited in claim 1 further comprising a loaded wheel driving system including an axis of rotation for turning a crank coupled to the loaded wheel and for selectively driving the loaded wheel at a selected back and forth movement frequency between 0.1 Hz and 25 Hz when cyclically moving on the test samples.

6. The loaded wheel tester as recited in claim 1 wherein the second transducer comprises a linear variable differential transformer horizontally connecting the frame and loaded wheel via string.

7. The loaded wheel tester of claim 1 for conducting a viscoelastic property test and outputting a phase angle over time for the block test sample of pavement mixture.

8. The loaded wheel tester of claim 1 further comprising an environmental chamber whereby environmental temperature of a particular block test sample of a pavement mixture may be selectively controlled to a predetermined temperature within a range of temperatures between 100 C and 40" C and wherein the display is configured to display a graph over time of dynamic complex modulus at first and second different loading frequencies selected between a range of 0.1 Hz and 25 Hz and first and second different temperatures for the particular block test sample of pavement mixture within a range of temperatures between 10″ C and 400 C.

9. The loaded wheel tester of claim 1 wherein the display is further configured to display a graph of phase angle versus reduced frequency for comparing different block test samples of pavement mixtures.

10. A method of testing a viscoelastic property of an asphalt mixture test sample using a loaded wheel tester including a special purpose computer processor, the method characterized by:

the special purpose computer processor determining a position of a loaded wheel moving cyclically at varying frequency in relation to a lengthwise direction of a block test sample of pavement mixture having length, width and depth, the position measuring being responsive to receiving sensed inputs for measuring a phase angle, and the processor also calculating stress from wheel position and measuring strain over time in a direction orthogonal to a vertical nodal force place on the central axis of the loaded wheel via a transducer mounted on the bottom side center of the block test sample; and a display device, responsive to the special purpose computer processor, displaying a graph of the measured stress versus strain as a hysteresis loop over time.

11. The method of viscoelastic property testing according to claim 10 further comprising graphing the stress and strain over time at selected frequencies of cyclical movement between 0.1 Hz and 25 Hz and using a fast Fourier transform for data smoothing.

12. The method of viscoelastic testing according to claim 11 further comprising testing different test samples of pavement mixtures simultaneously and graphing dynamic modulus versus reduced frequency for comparing the different test samples of pavement mixtures.

13. The method of viscoelastic testing according to claim 10 further comprising testing different test samples of asphalt mixtures simultaneously and graphing creep compliance, the creep compliance graph being displayed on a display device responsive to the special purpose computer processor and the creep compliance graph comparing creep compliance of a plurality of the different test samples of different asphalt mixtures.

* * * * *